United States Patent
Wen et al.

(10) Patent No.: US 10,017,798 B2
(45) Date of Patent: Jul. 10, 2018

(54) *E. COLI* ENGINEERING BACTERIA PRODUCING 1,5-PENTANEDIAMINE THROUGH WHOLE CELL CATALYSIS AND APPLICATION THEREOF

(71) Applicant: INSTITUTE OF MICROBIOLOGY, CHINESE ACADEMY OF SCIENCES, Beijing (CN)

(72) Inventors: Tingyi Wen, Beijing (CN); Shuwen Liu, Beijing (CN); Yong Liang, Beijing (CN); Xiuling Shang, Beijing (CN); Qian Liu, Beijing (CN); Jifu Wen, Beijing (CN); Yun Zhang, Beijing (CN)

(73) Assignee: NINGXIA EPPEN BIOTECH CO., LTD, Yin Chuan, Ning Xia (CN)

( * ) Notice: Subject to any disclaimer, the term of this patent is extended or adjusted under 35 U.S.C. 154(b) by 0 days.

(21) Appl. No.: 15/122,340

(22) PCT Filed: Jun. 25, 2015

(86) PCT No.: PCT/CN2015/082400
§ 371 (c)(1),
(2) Date: Aug. 29, 2016

(87) PCT Pub. No.: WO2015/197014
PCT Pub. Date: Dec. 30, 2015

(65) Prior Publication Data
US 2017/0226544 A1    Aug. 10, 2017

(30) Foreign Application Priority Data

Jun. 27, 2014  (CN) .......................... 2014 1 0302561

(51) Int. Cl.
| C12N 1/20 | (2006.01) |
| C12P 13/00 | (2006.01) |
| C12N 9/88 | (2006.01) |

(52) U.S. Cl.
CPC .............. *C12P 13/001* (2013.01); *C12N 9/88* (2013.01); *C12Y 401/01018* (2013.01)

(58) Field of Classification Search
CPC .. C12N 9/88; C12P 13/001; C12Y 401/01018
USPC ................................... 435/128, 252.3, 320.1
See application file for complete search history.

(56) References Cited

U.S. PATENT DOCUMENTS 9,745,608 B2 *  8/2017  Wittmann ................ C12N 9/88

OTHER PUBLICATIONS

PCT.CN2015.082400.WO2015197014(written opnion), dated 2015.*

* cited by examiner

*Primary Examiner* — Tekchand Saidha
(74) *Attorney, Agent, or Firm* — Li&Cai Intellectual Property (USA) Office

(57) ABSTRACT

The present invention discloses an *E. coli* engineering bacteria producing 1,5pentanediamine through a whole cell catalysis and its application. The engineering bacteria according to the present invention, is *Escherichia coli* (*E. coli*) strain B or its derivative strains with the overexpression of a lysine decarboxylase gene and a proper expression of a lysinecadaverine antiporter gene cadB. The engineering bacteria according to the present invention is the engineering bacteria producing 1,5pentanediamine through the whole cell catalysis constructed from *Escherichia coli* B derivative strains, which has an overexpression of a lysine decarboxylase gene cadA and a proper expression of the lysinecadaverine antiporter gene cadB; The present invention further discloses a method of producing a 1,5pentanediamine catalyzed by the engineering bacteria, the yield and production intensity of 1,5pentanediamine in biobased production could be significantly improved through the method, hence it could be applied to mass production and convenient for extending applications.

11 Claims, 5 Drawing Sheets

SEQUENCE LISTING

<160> NUMBER OF SEQ ID NOS: 29

<210> SEQ ID NO 1
<211> LENGTH: 2148
<212> TYPE: DNA
<213> ORGANISM: E.coli K12 W3110

<400> SEQUENCE: 1

```
atgaacgtta ttgcaatatt gaatcacatg ggggtttatt ttaaagaaga acccatccgt      60
gaacttcatc gcgcgcttga acgtctgaac ttccagattg tttacccgaa cgaccgtgac    120
gacttattaa aactgatcga aaacaatgcg cgtctgtgcg gcgttatttt tgactgggat    180
aaatataatc tcgagctgtg cgaagaaatt agcaaaatga acgagaacct gccgttgtac    240
gcgttcgcta atacgtattc cactctcgat gtaagcctga atgacctgcg tttacagatt    300
agcttctttg aatatgcgct gggtgctgct gaagatattg ctaataagat caagcagacc    360
actgacgaat atatcaacac tattctgcct ccgctgacta aagcactgtt taaatatgtt    420
cgtgaaggta aatatacttt ctgtactcct ggtcacatgg gcggtactgc attccagaaa    480
agcccggtag gtagcctgtt ctatgatttc tttggtccga ataccatgaa atctgatatt    540
tccatttcag tatctgaact gggttctctg ctggatcaca gtggtccaca caaagaagca    600
gaacagtata tcgctcgcgt ctttaacgca gaccgcagct acatggtgac caacggtact    660
tccactgcga acaaaattgt tggtatgtac tctgctccag caggcagcac cattctgatt    720
gaccgtaact gccacaaatc gctgacccac ctgatgatga tgagcgatgt tacgccaatc    780
tatttccgcc cgacccgtaa cgcttacggt attcttggtg gtatcccaca gagtgaattc    840
cagcacgcta ccattgctaa gcgcgtgaaa gaaacaccaa acgcaacctg gccggtacat    900
gctgtaatta ccaactctac ctatgatggt ctgctgtaca caccgactt catcaagaaa    960
acactggatg tgaaatccat ccactttgac tccgcgtggg tgccttacac caacttctca   1020
ccgatttacg aaggtaaatg cggtatgagc ggtggccgtg tagaagggaa agtgatttac   1080
gaaacccagt ccactcacaa actgctggcg gcgttctctc aggcttccat gatccacgtt   1140
aaaggtgacg taaacgaaga aaccttaacg gaagcctaca tgatgcacac caccacttct   1200
ccgcactacg gtatcgtggc gtccactgaa accgctgcgg cgatgatgaa aggcaatgca   1260
ggtaagcgtc tgatcaacgg ttctattgaa cgtgcgatca attccgtaa agagatcaaa   1320
cgtctgagaa cggaatctga tggctggttc tttgatgtat ggcagccgga tcatatcgat   1380
acgactgaat gctggccgct gcgttctgac agcacctggc acggcttcaa aaacatcgat   1440
aacgagcaca tgtatcttga cccgatcaaa gtcaccctgc tgactccggg gatggaaaaa   1500
gacggcacca tgagcgactt tggtattccg gccagcatcg tggcgaaata cctcgacgaa   1560
catggcatcg ttgttgagaa aaccggtccg tataacctgc tgttcctgtt cagcatcggt   1620
atcgataaga ccaaagcact gagcctgctg cgtgctctga ctgactttaa acgtgcgttc   1680
gacctgaacc tgcgtgtgaa aaacatgctg ccgtctctgt atcgtgaaga tcctgaattc   1740
tatgaaaaca tgcgtattca ggaactggct cagaatatcc acaaactgat tgttcaccac   1800
aatctgccgg atctgatgta tcgcgcattt gaagtgctgc cgacgatggt aatgactccg   1860
```

| | |
|---|---|
| tatgctgcat tccagaaaga gctgcacggt atgaccgaag aagtttacct cgacgaaatg | 1920 |
| gtaggtcgta ttaacgccaa tatgatcctt ccgtacccgc cgggagttcc tctggtaatg | 1980 |
| ccgggtgaaa tgatcaccga agaaagccgt ccggttctgg agttcctgca gatgctgtgt | 2040 |
| gaaatcggcg ctcactatcc gggctttgaa accgatattc acggtgcata ccgtcaggct | 2100 |
| gatggccgct ataccgttaa ggtattgaaa gaagaaagca aaaaataa | 2148 |

<210> SEQ ID NO 2
<211> LENGTH: 1335
<212> TYPE: DNA
<213> ORGANISM: E.coli K12 W3110

<400> SEQUENCE: 2

| | |
|---|---|
| atgagttctg ccaagaagat cgggctattt gcctgtaccg gtgttgttgc cggtaatatg | 60 |
| atggggagcg gtattgcatt attacctgcg aacctagcaa gtatcggtgg tattgctatc | 120 |
| tggggttgga ttatctctat tattggtgca atgtcgctgg cgtatgtata tgcccgactg | 180 |
| gcaacaaaaa acccgcaaca aggtggccca attgcttatg ccgagaaaat ttcccctgca | 240 |
| tttggttttc agacaggtgt tctttattac catgctaact ggattggtaa cctggcgatt | 300 |
| ggtattaccg ctgtatctta tctttccacc ttcttcccag tattaaatga tcctgttccg | 360 |
| gcgggtatcg cctgtattgc tatcgtctgg gtatttacct ttgtaaatat gctcggcggt | 420 |
| acttgggtaa gccgtttaac cactattggt ctggtgctgg ttcttattcc tgtggtgatg | 480 |
| actgctattg ttggctggca ttggtttgat gcggcaactt atgcagctaa ctggaatact | 540 |
| gcggatacca ctgatggtca tgcgatcatt aaaagtattc tgctctgcct gtgggccttc | 600 |
| gtgggtgttg aatccgcagc tgtaagtact ggtatggtta aaaacccgaa acgtaccgtt | 660 |
| ccgctggcaa ccatgctggg tactggttta gcaggtattg tttacatcgc tgcgactcag | 720 |
| gtgctttccg gtatgtatcc gtcttctgta atggcggctt ccggtgctcc gtttgcaatc | 780 |
| agtgcttcaa ctatcctcgg taactgggct gcgccgctgg tttctgcatt caccgccttt | 840 |
| gcgtgcctga cttctctggg ctcctggatg atgttggtag gccaggcagg tgtacgtgcc | 900 |
| gctaacgacg gtaacttccc gaaagtttat ggtgaagtcg acagcaacgg tattccgaaa | 960 |
| aaaggtctgc tgctggctgc agtgaaaatg actgccctga tgatccttat cactctgatg | 1020 |
| aactctgccg gtggtaaagc atctgacctg ttcggtgaac tgaccggtat cgcagtactg | 1080 |
| ctgactatgc tgccgtattt ctactcttgc gttgacctga ttcgttttga aggcgttaac | 1140 |
| atccgcaact tgtcagcct gatctgctct gtactgggtt gcgtgttctg cttcatcgcg | 1200 |
| ctgatgggcg caagctcctt cgagctggca ggtaccttca tcgtcagcct gattatcctg | 1260 |
| atgttctacg ctcgcaaaat gcacgagcgc cagagccact caatggataa ccacaccgcg | 1320 |
| tctaacgcac attaa | 1335 |

<210> SEQ ID NO 3
<211> LENGTH: 9
<212> TYPE: DNA
<213> ORGANISM: Artificial sequence
<220> FEATURE:
<223> OTHER INFORMATION: the sequence is synthesized

<400> SEQUENCE: 3

| | |
|---|---|
| ctaggaagt | 9 |

<210> SEQ ID NO 4
<211> LENGTH: 510
<212> TYPE: DNA
<213> ORGANISM: Artificial sequence
<220> FEATURE:
<223> OTHER INFORMATION: the sequence is synthesized

<400> SEQUENCE: 4

| | | | | | |
|---|---|---|---|---|---|
| cgcggatcct | gcgccattct | caacatcctt | tagatgaaaa | acaattagca gcactgaaca | 60 |
| cagaaataga | taacattgtt | acactaccgg | aattgaataa | cctgtccatt atatatcaaa | 120 |
| taaaagcggt | cagtgctctg | gtaaaaggta | aaacagatga | gtcttaccag gcgataaata | 180 |
| ctggcattga | tcttgaaatg | tcctggctaa | attatgtatt | gcttggcaag gtttatgaaa | 240 |
| tgaaggggat | gaaccgggaa | gcggctgatg | catatctcac | cgcctttaat ttacgcccag | 300 |
| gggcaaacac | cctttactgg | attgaaaatg | gtatattcca | gacttctgtt ccttatgttg | 360 |
| taccttatct | cgacaaattt | ctcgcttcag | aataagtaac | tcccggggttg atttatgctc | 420 |
| ggcaatattt | gttgttgagt | ttttgtatgt | tactgttggt | ataatatgtt gcggcataat | 480 |
| acgactcact | ataggggaat | tgtgagcgga | | | 510 |

<210> SEQ ID NO 5
<211> LENGTH: 610
<212> TYPE: DNA
<213> ORGANISM: Artificial sequence
<220> FEATURE:
<223> OTHER INFORMATION: the sequence is synthesized

<400> SEQUENCE: 5

| | | | | | |
|---|---|---|---|---|---|
| actcactata | ggggaattgt | gagcggataa | caattccgaa | attaggagaa gagcatgagt | 60 |
| tctgccaaga | agatcgggct | atttgcctgt | accggtgttg | ttgccggtaa tatgatgggg | 120 |
| agcggtattg | cattattacc | tgcgaaccta | gcaagtatcg | gtggtattgc tatctggggt | 180 |
| tggattatct | ctattattgg | tgcaatgtcg | ctggcgtatg | tatatgcccg actggcaaca | 240 |
| aaaaacccgc | aacaaggtgg | cccaattgct | tatgccggag | aaatttcccc tgcatttggt | 300 |
| tttcagacag | gtgttcttta | ttaccatgct | aactggattg | gtaacctggc gattggtatt | 360 |
| accgctgtat | cttatctttc | caccttcttc | ccagtattaa | atgatcctgt tccggcgggt | 420 |
| atcgcctgta | ttgctatcgt | ctgggtatttt | accttgtaa | atatgctcgg cggtacctgg | 480 |
| gtaagccgtt | taaccactat | tggtctggtg | ctggttcttta | ttcctgtggt gatgactgct | 540 |
| attgttggct | ggcattggtt | tgatgcggca | acttatgcag | ctaactggaa tactgcggag | 600 |
| cggccgcaat | | | | | 610 |

<210> SEQ ID NO 6
<211> LENGTH: 41
<212> TYPE: DNA
<213> ORGANISM: Artificial sequence
<220> FEATURE:
<223> OTHER INFORMATION: the sequence is synthesized
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t

```
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t

<400> SEQUENCE: 6
catgccatgg cagtnatngc aatattnaat canatgggng t                    41

<210> SEQ ID NO 7
<211> LENGTH: 36
<212> TYPE: DNA
<213> ORGANISM: Artificial sequence
<220> FEATURE:
<223> OTHER INFORMATION: the sequence is synthesized

<400> SEQUENCE: 7
acgcgtcgac ctccttatga gcaaaaaagg gaagtg                          36

<210> SEQ ID NO 8
<211> LENGTH: 33
<212> TYPE: DNA
<213> ORGANISM: Artificial sequence
<220> FEATURE:
<223> OTHER INFORMATION: the sequence is synthesized

<400> SEQUENCE: 8
tgctctagaa cctggagata tgactatgaa cgt                             33

<210> SEQ ID NO 9
<211> LENGTH: 38
<212> TYPE: DNA
<213> ORGANISM: Artificial sequence
<220> FEATURE:
<223> OTHER INFORMATION: the sequence is synthesized

<400> SEQUENCE: 9
catgccatgg ttattgcaat attgaatcac atgggggt                        38

<210> SEQ ID NO 10
<211> LENGTH: 41
<212> TYPE: DNA
<213> ORGANISM: Artificial sequence
<220> FEATURE:
<223> OTHER INFORMATION: the sequence is synthesized

<400> SEQUENCE: 10
catgccatgg cagttatagc aatattgaat catatgggag t                    41

<210> SEQ ID NO 11
<211> LENGTH: 41
<212> TYPE: DNA
<213> ORGANISM: Artificial sequence
<220> FEATURE:
<223> OTHER INFORMATION: the sequence is synthesized

<400> SEQUENCE: 11
catgccatgg cagttatagc aatattgaat cacatggggg t                    41

<210> SEQ ID NO 12
<211> LENGTH: 41
<212> TYPE: DNA
<213> ORGANISM: Artificial sequence
```

```
<220> FEATURE:
<223> OTHER INFORMATION: the sequence is synthesized

<400> SEQUENCE: 12
catgccatgg cagttatagc aatattaaat cacatggggg t        41

<210> SEQ ID NO 13
<211> LENGTH: 41
<212> TYPE: DNA
<213> ORGANISM: Artificial sequence
<220> FEATURE:
<223> OTHER INFORMATION: the sequence is synthesized

<400> SEQUENCE: 13
catgccatgg cagttattgc aatattgaat cacatgggag t        41

<210> SEQ ID NO 14
<211> LENGTH: 41
<212> TYPE: DNA
<213> ORGANISM: Artificial sequence
<220> FEATURE:
<223> OTHER INFORMATION: the sequence is synthesized

<400> SEQUENCE: 14
catgccatgg cagttattgc aatattgaat catatgggag t        41

<210> SEQ ID NO 15
<211> LENGTH: 41
<212> TYPE: DNA
<213> ORGANISM: Artificial sequence
<220> FEATURE:
<223> OTHER INFORMATION: the sequence is synthesized

<400> SEQUENCE: 15
catgccatgg cagttattgc aatattgaat cacatggggg t        41

<210> SEQ ID NO 16
<211> LENGTH: 41
<212> TYPE: DNA
<213> ORGANISM: Artificial sequence
<220> FEATURE:
<223> OTHER INFORMATION: the sequence is synthesized

<400> SEQUENCE: 16
catgccatgg cagttattgc aatattaaat cacatggggg t        41

<210> SEQ ID NO 17
<211> LENGTH: 41
<212> TYPE: DNA
<213> ORGANISM: Artificial sequence
<220> FEATURE:
<223> OTHER INFORMATION: the sequence is synthesized

<400> SEQUENCE: 17
catgccatgg cagttattgc aatattaaat catatgggag t        41

<210> SEQ ID NO 18
<211> LENGTH: 32
<212> TYPE: DNA
<213> ORGANISM: Artificial sequence
<220> FEATURE:
<223> OTHER INFORMATION: the sequence is synthesized

<400> SEQUENCE: 18
catgccatgg gttctgccaa gaagatcggg ct        32
```

<210> SEQ ID NO 19
<211> LENGTH: 35
<212> TYPE: DNA
<213> ORGANISM: Artificial sequence
<220> FEATURE:
<223> OTHER INFORMATION: the sequence is synthesized

<400> SEQUENCE: 19
cccaagcttg caagccactt cccttgtacg agcta                          35

<210> SEQ ID NO 20
<211> LENGTH: 30
<212> TYPE: DNA
<213> ORGANISM: Artificial sequence
<220> FEATURE:
<223> OTHER INFORMATION: the sequence is synthesized

<400> SEQUENCE: 20
cccaagcttt gaaattagga gaagagcatg                                30

<210> SEQ ID NO 21
<211> LENGTH: 39
<212> TYPE: DNA
<213> ORGANISM: Artificial sequence
<220> FEATURE:
<223> OTHER INFORMATION: the sequence is synthesized

<400> SEQUENCE: 21
cccaagcttc taggaagtag agcatgagtt ctgccaaga                      39

<210> SEQ ID NO 22
<211> LENGTH: 37
<212> TYPE: DNA
<213> ORGANISM: Artificial sequence
<220> FEATURE:
<223> OTHER INFORMATION: the sequence is synthesized

<400> SEQUENCE: 22
ataagaatgc ggccgcttaa tgtgcgttag acgcggt                        37

<210> SEQ ID NO 23
<211> LENGTH: 30
<212> TYPE: DNA
<213> ORGANISM: Artificial sequence
<220> FEATURE:
<223> OTHER INFORMATION: the sequence is synthesized

<400> SEQUENCE: 23
cgcggatcct gcgccattct caacatcctt                                30

<210> SEQ ID NO 24
<211> LENGTH: 58
<212> TYPE: DNA
<213> ORGANISM: Artificial sequence
<220> FEATURE:
<223> OTHER INFORMATION: the sequence is synthesized

<400> SEQUENCE: 24
tccgctcaca attcccctat agtgagtcgt attatgccgc aacatattat accaacag         58

<210> SEQ ID NO 25
<211> LENGTH: 59
<212> TYPE: DNA
<213> ORGANISM: Artificial sequence
<220> FEATURE:
<223> OTHER INFORMATION: the sequence is synthesized

<400> SEQUENCE: 25
actcactata ggggaattgt gagcggataa caattccgaa attaggagaa gagcatgag    59

<210> SEQ ID NO 26
<211> LENGTH: 32
<212> TYPE: DNA
<213> ORGANISM: Artificial sequence
<220> FEATURE:
<223> OTHER INFORMATION: the sequence is synthesized

<400> SEQUENCE: 26
attgcggccg ctccgcagta ttccagttag ct    32

<210> SEQ ID NO 27
<211> LENGTH: 20
<212> TYPE: DNA
<213> ORGANISM: Artificial sequence
<220> FEATURE:
<223> OTHER INFORMATION: the sequence is synthesized

<400> SEQUENCE: 27
taccgttgct gtcgacttca    20

<210> SEQ ID NO 28
<211> LENGTH: 20
<212> TYPE: DNA
<213> ORGANISM: Artificial sequence
<220> FEATURE:
<223> OTHER INFORMATION: the sequence is synthesized

<400> SEQUENCE: 28
ctccgtttgc aatcagtgct    20

<210> SEQ ID NO 29
<211> LENGTH: 1080
<212> TYPE: DNA
<213> ORGANISM: Artificial sequence
<220> FEATURE:
<223> OTHER INFORMATION: the sequence is synthesized

<400> SEQUENCE: 29
cgcggatcct gcgccattct caacatcctt tagatgaaaa acaattagca gcactgaaca    60
cagaaataga taacattgtt acactaccgg aattgaataa cctgtccatt atatatcaaa   120
taaaagcggt cagtgctctg gtaaaaggta aaacagatga gtcttaccag gcgataaata   180
ctggcattga tcttgaaatg tcctggctaa attatgtatt gcttggcaag gtttatgaaa   240
tgaaggggat gaaccgggaa gcggctgatg catatctcac cgcctttaat ttacgcccag   300
gggcaaacac cctttactgg attgaaaatg gtatattcca gacttctgtt ccttatgttg   360
taccttatct cgacaaattt ctcgcttcag aataagtaac tcccgggttg atttatgctc   420
ggcaatattt gttgttgagt ttttgtatgt tactgttggt ataatatgtt gcggcataat   480
acgactcact ataggggaat tgtgagcgga taacaattcc gaaattagga gaagagcatg   540
agttctgcca agaagatcgg gctatttgcc tgtaccggtg ttgttgccgg taatatgatg   600
gggagcggta ttgcattatt acctgcgaac ctagcaagta tcggtggtat tgctatctgg   660
ggttggatta tctctattat tggtgcaatg tcgctggcgt atgtatatgc ccgactggca   720
acaaaaaacc cgcaacaagg tggcccaatt gcttatgccg agaaatttc ccctgcattt   780 ggttttcaga caggtgttct ttattaccat gctaactgga ttggtaacct ggcgattggt   840
attaccgctg tatcttatct ttccaccttc ttcccagtat taaatgatcc tgttccggcg   900

-continued

```
ggtatcgcct gtattgctat cgtctgggta tttacctttg taaatatgct cggcggtacc    960
tgggtaagcc gtttaaccac tattggtctg gtgctggttc ttattcctgt ggtgatgact    1020
gctattgttg gctggcattg gtttgatgcg gcaacttatg cagctaactg gaatactgcg    1080
```

E. COLI ENGINEERING BACTERIA PRODUCING 1,5-PENTANEDIAMINE THROUGH WHOLE CELL CATALYSIS AND APPLICATION THEREOF

BACKGROUND OF THE INVENTION

1. Field of the Invention

The present invention relates to an *E. coli* engineering bacteria, in particular to an *E. coli* engineering bacteria producing 1,5pentanediamine through whole cell catalysis and application thereof.

2. Description of Related Art 1,5Pentanediamine, also known by the names Cadaverine and 1,5,Diaminopentane, could be used for synthesizing polymer polyamide (i.e. nylon) through polymerization with dicarboxylic acid. The global production of polyamide materials is about 7 million tons annually, which requires a huge consumption of petrochemical resources. Therefore, 1,5pentanediamine being the important component monomer of the polyamide is synthesized by a biological preparation that has important economic and ecological significances.

The biological preparation of 1,5pentanediamine now are mainly through the methods of microbial fermentation and catalysis, in which, glucose is used as a carbon source in the fermentation process, and a pentanediamine is synthesized through a series of metabolic pathways in a bacterial strain. The maximum yield is 88 g/L, and the production intensity is 2.2 g/L/h (Kind et al, Metabolic Engineering, 2014, 25:113123). Lysine is used as a substrate in the whole cell catalysis, and a lysine decarboxylase of the bacterial cell catalyzes to produce the pentanediamine. At present, lysine is one of the main bulk amino acids, which is overproduced, such that the profit margin is very low. Therefore, to development a highly efficient method for producing the pentanediamine through the biological catalysis method of which the lysine is used as a substrate. It could not only suitable for a new type of biobased materials market, but also could promote the transformation of and upgrading the amino acid fermentation industries.

In the prior art of producing the 1,5pentanediamine through a whole cell catalysis, the pUC18 was used as an over expression vector of the lysine decarboxylase gene cadA by Ajinomoto Co., Ltd., Japan (U.S. Pat. No. 7,189,543, EP1482055). The recombinant plasmid was transformed into an *Escherichia coli* (*E. coli*) K12 derived strain JM109, there was thus obtained the engineering bacteria producing the 1,5pentanediamine through the whole cell catalysis. Using the engineering bacteria to carry out the whole cell catalysis, the yield of pentanediamine after 11 h was 69 g/L, and the production intensity was about 6.2 g/L/h. In order to improve the catalytic performance of the engineering bacteria, technologies of heat treatment, freezing melting and ultrasonic treatments were used (CN 102782146) on the engineering bacterial cell. However, these treatments increase the process difficulty and cost in actual production.

At present, in the prior art of producing the 1,5pentanediamine through a biocatalysis, the catalytic performance is low, and the catalytic process is complex, which seriously limits the application of the 1,5pentanediamine in the industrial production.

SUMMARY OF THE INVENTION

The instant disclosure provide an *E. coli* engineering bacteria producing a 1,5pentanediamine through a whole cell catalysis and application thereof.

The engineering bacteria provided by the instant disclosure are an *Escherichia coli* (*E. coli*) strain B or one of its derivative strains that overexpress a lysine decarboxylase gene and properly express a lysinecadaverine antiporter gene cadB therein.

As for the above mentioned engineering bacteria, the method of overexpression of the lysine decarboxylase gene is to place a complete or a partial of nucleotide sequences of the lysine decarboxylase gene behind a promoter in exogenous expression plasmids for expression.

The proper expression of lysinecadaverine antiporter gene cadB is to places the complete or the partial of nucleotide sequences of said the lysinecadaverine antiporter gene with/ without a RBS sequence behind the nucleotide sequences of the lysine decarboxylase gene in the exogenous expression plasmids for expression, or, to replace a promoter of lysinecadaverine antiporter gene on a chromosome of the *E. coli* strain B or its derivative strains with a promoter capable of relieving a transcriptional repression of the CadB and suitable for the *E. coli*.

The promoter capable of relieving the transcriptional repression of the CadB and suitable for the *E. coli*, preferably, is an L promoter, a trc promoter, a T5 promoter, a lac promoter or a T7 promoter.

As for any of the above mentioned engineering bacteria, the lysine decarboxylase gene is a modified lysine decarboxylase gene cadA, a modification is to replace a second codon of the lysine decarboxylase gene cadA with a GCA, and then to replace No. +7 to +33 base sequences of the lysine decarboxylase gene cadA with synonymous codons so as to increase the number of rare codons as well as selecting a sequence of posttranscriptional mRNA whose secondary structure with a low minimal free energy and a high translation initiation efficiency.

Preferably, the No. +1 to +35 base sequences of the modified lysine decarboxylase gene cadA are as follows:

```
              (the residues 7-41 of SEQ ID NO. 10)
5'-ATGGCAGTTATAGCAATATTGAATCATATGGGAGT-3'

(the residues 7-41 of SEQ ID NO. 11)
5'-ATGGCAGTTATAGCAATATTGAATCACATGGGGGT-3'

(the residues 7-41 of SEQ ID NO. 12)
5'-ATGGCAGTTATAGCAATATTAAATCACATGGGGGT-3'

(the residues 7-41 of SEQ ID NO. 13)
5'-ATGGCAGTTATTGCAATATTGAATCACATGGGAGT-3'

(the residues 7-41 of SEQ ID NO. 14)
5'-ATGGCAGTTATTGCAATATTGAATCATATGGGAGT-3'

(the residues 7-41 of SEQ ID NO. 15)
5'-ATGGCAGTTATTGCAATATTGAATCACATGGGGGT-3'

(the residues 7-41 of SEQ ID NO. 16)
5'-ATGGCAGTTATTGCAATATTAAATCACATGGGGGT-3'

(the residues 7-41 of SEQ ID NO. 17)
5'-ATGGCAGTTATTGCAATATTAAATCATATGGAGT-3'.
```

As for any of the above mentioned engineering bacteria, the *Escherichia coli* strain B is an *Escherichia coli* BL21 (DE3).

As for any of the above mentioned engineering bacteria, the method for the overexpression of the lysine decarboxylase gene and the proper expression of the lysinecadaverine antiporter gene cadB in the *Escherichia coli* (*E. coli*) strain B or its derivative strains is realized by means of the following (1) or (2):

(1) Introducing an encoding gene of a lysine decarboxylase and encoding segments of the lysinecadaverine antiporter gene containing a $RBS_{BCD22}$ into the E. coli strain B or its derivative strains.

The segment was introduced through a recombinant expression vector.

The recombinant expression vector was obtained by inserting the segment between a multiple cloning loci of pET28a (+).

The construction of the recombinant expression vector is specifically as follows: inserting the encoding segment containing the lysine decarboxylase gene into the vector pET28a(+) between loci of Nco I and Sal I, there being thus obtained a recombinant expression vector 1, and then inserting the encoding segment of lysinecadaverine antiporter gene containing the $RBS_{BCD22}$ into the recombinant expression vector 1 between the loci of Not I and Hind III.

The nucleotide sequence of the encoding segment of lysinecadaverine antiporter gene is shown as SEQ ID No.2.

The nucleotide sequence of the $RBS_{BCD22}$ is shown as SEQ ID No.3.

(2) Replacing a promoter of operon cadBA in the E. coli strain B or its derivative strains with the promoter capable of relieving the transcriptional repression of CadB and suitable for E. coli, and then inserting the encoding segment containing the lysine decarboxylase gene into the E. coli strain B or its derivative strains, or inserting one or more modified cadB gene whose promoter has been replaced into other loci on the chromosome.

Replacing the promoter of operon cadBA in the E. coli strain B or its derivative strains with the T7 promoter is as follows: Introducing a plasmid of lysinecadaverine antiporter encoding gene containing the T7 promoter into the E. coli strain B or its derivative strains to carry out a homologous recombination.

The plasmid of lysinecadaverine antiporter encoding gene containing T7 promoter is obtained by inserting the lysinecadaverine antiporter encoding gene containing T7 promoter into a plasmid pKOV between loci of BamHI and Not I.

A segment containing the encoding gene of lysine decarboxylase protein was introduced through the recombinant expression vector.

The recombinant expression vector was obtained by inserting the segment between the multiple cloning loci of pET28a (+).

The recombinant expression vector is constructed specifically as follows: inserting the encoding segment containing the lysine decarboxylase gene into the vector pET28a(+) between the loci of Nco I and Sal I.

The nucleotide sequence of the encoding gene of the lysine decarboxylase protein is shown as SEQ ID No. 1.

The segment of the lysine decarboxylase protein encoding gene is shown as SEQ ID No.1.

A method for preparing a 1,5pentanediamine is also protected by the scope of the instant disclosure, including the following steps: culturing any of the above mentioned engineering bacteria in a LB liquid medium containing kanamycin, and a seed solution being obtained; inoculating the seed solution into a rich medium for a fermentation culture; adding an inducer to induce an expression, adding a substrate lysine and a vitamin B6 directly into the culture medium, or adding the substrate lysine and the vitamin B6 after the bacterial cells being collected and removed from a fermentation broth to initial a whole cell catalysis.

The inducer is specifically a IPTG or a lactose.

The substrate lysine is specifically the lysine fermentation broth containing a lysine producing bacteria, a bacterial cells removed lysine fermentation broth, a decolored bacterial cells removed lysine fermentation broth, an ion exchange elution of the lysine fermentation broth, a free lysine, and a lysine powder or a lysine solution.

The vitamin B6 is a pyridoxal, a pyridoxal phosphate and/or a pyridoxal hydrochloride.

The rich medium contains 10 g/L yeast extract, 20 g/L peptone, 0.9 g/L $K_2HPO_4.3H_2O$, 1.14 g/L $KH_2PO_4$, 10 g/L $(NH_4)_2SO_4$, 0.3 g/L $MgSO_4.7H_2O$, 5 mL/L trace elements stock solution, 50 mg/L kanamycin, and water for the rest.

The trace elements stock solution contains 6 g/L $FeSO_4.7H_2O$, 1.35 g/L $CaCl_2$, 0.8 g/L $ZnSO_4.7H_2O$, 1.5 g/L $MnSO_4.4H_2O$, 0.15 g/L $CuSO_4.5H_2O$, 0.2 g/L $(NH_4)_6Mo_7O_{24}.4H_2O$, 0.1 g/L $H_3BO_3$, 0.25 g/L $CoCl_2.6H_2O$, 10 mL/L HCl (concentrated), and water for the rest.

In the above method, the concentration of kanamycin in the liquid LB medium is in a range of 5200 mg/L, and specifically is 50 mg/L.

An $OD_{600}$ value of the seed solution is 225, and preferably is 35.

The seed solution is inoculated into the rich medium in a volume percentage range of 0.530%, and specifically is 5%.

A fermentation temperature is in a range of 2545° C., and specifically is 37° C.

ADO of the fermentation culture is above 50%.

A pH value of the fermentation culture is in a range of 4.09.0.

A final concentration of the IPTG is in a range of 0.0110 mM, and preferably is in a range of 0.050.4 mM.

A time of adding the IPTG is in a range of 210 h after the fermentation, and preferably is in a range of 26 h.

An induce of IPTG includes a step of supplementing a glucose at a rate that is in a range of 0.510 g/L, and specifically is 3 g/L.

The lysine includes an Llysine hydrochloride or a lysine sulfate.

A time of adding the substrate lysine and the vitamin B6 to initial the whole cell catalysis is in a range of 0.510 h after the induction, and preferably is 15 h.

A pH value in the catalytic process is maintained in a range of 4.010.0.

An acid solution for adjusting the pH value could be an inorganic acid or an organic acid, the inorganic acid could be a hydrochloric acid, a sulfuric acid, a phosphoric acid or a nitric acid, and the organic acid could be an adipic acid, a succinic acid, a sebacic acid, an acetic acid, or a lactic acid.

The catalysis also includes the following steps: supplementing a glucose at a rate that is in a range of 0.510 g/L, conducting an aeration rate that is in a range of 010 vvm, controlling a temperature that is in a range of 2560° C., and conducting a rotation speed that is in a range of 01200 rpm.

In the catalytic process, the rate of supplementing the glucose is specifically in a range of 02 g/L.

In the catalytic process, the aeration rate is in a range of 0.55 vvm.

In the catalytic process, the temperature is specifically in a range of 3050° C.

In the catalytic process, a stirrer speed is specifically in a range of 2001000 rpm.

A method for preparing a 1,5pentanediamine is also protected by the scope of the instant disclosure, including the following steps: culturing the engineering bacteria according to any of the abovementioned descriptions of the LB liquid medium containing the kanamycin, and obtaining the seed solution; inoculating the seed solution into a minimal medium for a fermentation culture; adding an inducer to induce an expression, adding a substrate lysine and a vitamin B6 directly into a culture medium, or adding the substrate lysine and the vitamin B6 after the bacterial cells being collected and removed from a fermentation broth to initial a whole cell catalysis.

The inducer is an IPTG or a lactose.

The substrate lysine is the lysine fermentation broth containing a lysine producing bacteria, a bacterial cells removed lysine fermentation broth, a decolored bacterial cells removed lysine fermentation broth, an ion exchange elution of the lysine fermentation broth, a free lysine, and a lysine powder or a lysine solution.

The vitamin B6 is a pyridoxal, a pyridoxal phosphate and a pyridoxal hydrochloride.

The minimal medium contains 2 g/L $(NH_4)_2HPO_4$, 4 g/L $KH_2PO_4$, 0.85 g/L citric acid, 0.7 g/L $MgSO_4.7H_2O$, 10 mg/L $FeSO_4.7H_2O$, 2.25 mg/L $ZnSO_4.7H_2O$, 0.2 mg/L $CuSO_4.5H_2O$, 0.5 mg/L $MnSO_4.5H_2O$, 0.23 mg/L $NaB_4O_7.10H_2O$, 2.0 mg/L $CaCl_2.2H_2O$, 0.1 mg/L $NH_4Mo_7O_{24}$, 0.15 mg/L $CoCl_2.6H_2O$, and water for the rest.

In the above method, the concentration of kanamycin in the liquid LB medium is in a range of 5200 mg/L, and specifically is 50 mg/L.

An $OD_{600}$ value of the seed solution is in a range of 225, and preferably is in a range of 35.

A percentage of minimal medium inoculated into the seed solution is in a range of 0.530%, and specifically is 2%.

A fermentation temperature is in a range of 2545° C., and specifically is 37° C.

ADO of the fermentation culture is above 50%.

A concentration of a glucose during fermentation culture is maintained below 5 g/L, in particular realized by adding a feeding fluid in a Fedbatch fermentation, the feeding fluid containing 700 g/L glucose and 20 g/L $MgSO_4.7H_2O$, and water for the rest.

A final concentration of the IPTG is in a range of 0.0110 mM, and preferably is in a range of 0.050.4 mM.

A time of adding the IPTG is in a range of 320 h after the fermentation, and preferably is in a range of 412 h.

A lysine salt includes an Llysine hydrochloride or a lysine sulfate.

A time of adding the substrate lysine and the vitamin B6 to initial the whole cell catalysis is in a range of 0.524 h after the induction, and specifically is in a range of 15 h.

A pH value of the catalytic process is maintained in a range of 4.010.0, and specifically is 6.5.

An acid solution for adjusting the pH value could be an inorganic acid or an organic acid, the inorganic acid could be a hydrochloric acid, a sulfuric acid, a phosphoric acid or a nitric acid and the organic acid could be an adipic acid, a succinic acid, a sebacic acid, an acetic acid, or a lactic acid.

The catalysis also including the following steps: supplementing an additional glucose at a rate that is in a range of 0.510 g/L, conducting an aeration rate that is in a range of 010 vvm, controlling a temperature that is in a range 2560° C., and conducting a rotation speed that is in a range of 01200 rpm.

In the catalytic process, the rate of supplementing the glucose is specifically in a range of 02 g/L.

In the catalytic process, the aeration rate is in a range of 0.55 vvm.

In the catalytic process, the temperature is specifically in a range of 3050° C.

A stirrer speed is specifically in a range of 2001000 rpm.

The applications of any engineering bacteria mentioned above in the preparation of a 1,5pentanediamine is also protected by the scope of the instant disclosure.

The applications of any engineering bacteria mentioned above in the preparation of a 1,5pentanediamine through catalysis of a substrate lysine and a vitamin B6 is also protected by the scope of the instant disclosure.

The substrate lysine is specifically the lysine fermentation broth containing a lysine producing bacteria, a bacterial cells removed lysine fermentation broth, a decolored bacterial cells removed lysine fermentation broth, an ion exchange elution of the lysine fermentation broth, a free lysine, and a lysine powder or a lysine solution, and more specifically an Llysine hydrochloride.

The vitamin B6 is specifically a pyridoxal, a pyridoxal phosphate and/or a pyridoxal hydrochloride.

An operon of the 1,5pentanediamine in the *E. coli* includes an inducible promoter $P_{cadB}$, a lysinecadaverine antiporter gene cadB, and a lysine decarboxylase gene cadA. With a low pH values and a high lysine concentration, an upstream regulatory gene cadC of the 1,5pentanediamine operon is activated, its product functions to the promoter $P_{cadB}$, and activates an expression of a lysine decarboxylase CadA and a lysinecadaverine antiporter CadB. The CadA catalyzes a synthesized 1,5pentanediamine in the *E. coli* cells, while the CadB transports the synthesized 1,5pentanediamine outside of the *E. coli* cells. (J Bacteriol, 1992, 174(8): 26592669.).

Different from the prior art which the *E. coli* engineering bacteria producing the 1,5pentanediamine through the whole cell catalysis is constructed starting from an *E. coli* K12 derivatives strain, in the instant disclosure, the *E. coli* engineering bacteria producing the 1,5pentanediamine through the whole cell catalysis is constructed starting from an *E. coli* strain B, which is suitable for a high efficient protein expression. In the instant disclosure, by an overexpression of a lysine decarboxylase gene and a proper expression of a lysinecadaverine antiporter gene cadB in the *E. coli* strain B or its derivative strains, the inhibition problem of bacterial growth is solved, and a catalytic performance of the 1,5pentanediamine is improved significantly. The instant disclosure further provides a method for producing the 1,5pentanediamine by using the engineering bacteria through the whole cell catalysis, a production yield of the 1,5pentanediamine could be in a range of 100300 g/L, and a production intensity of the 1,5pentanediamine could be in a range of 50300 g/L/h, which realized a 1,5pentanediamine production through the catalysis with a high production intensity and a high yield. Compared with the prior arts, the production yield and production rate of pentanediamine are increased many times by using the technology in the instant disclosure. The cost for producing the 1,5pentanediaminein is reduced, thus it could be applied to mass production of the 1,5pentanediaminein in practice, and it is convenient for extending applications.

In order to further appreciate the characteristics and technical contents of the instant disclosure, references are hereunder made to the detailed descriptions and appended drawings in connection with the instant disclosure. However, the appended drawings are merely shown for exemplary purposes, rather than being used to restrict the scope of the instant disclosure.

DETAILED DESCRIPTION OF THE PREFERRED EMBODIMENTS

Figure 1:
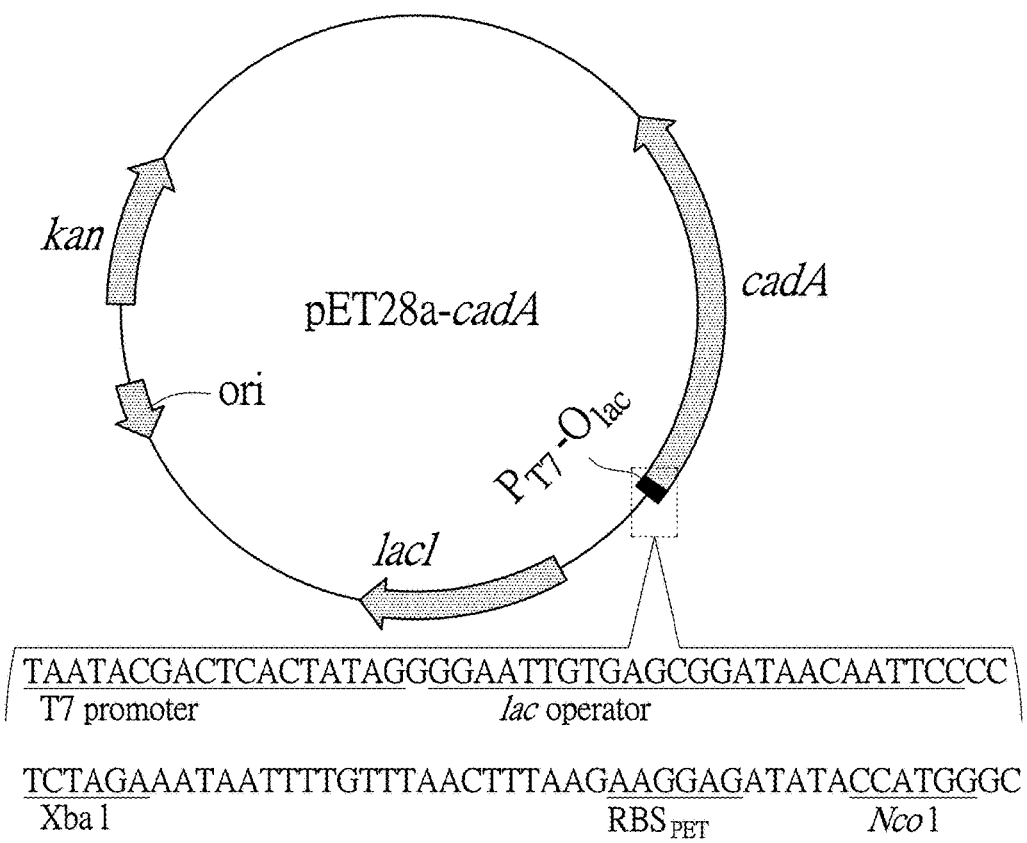
FIG. 1 is a schematic diagram of a plasmid pET28acadA.

Embodiments disclosed in the instant disclosure are illustrated via specific examples as follows, and people familiar in the art may easily understand the advantages and efficacies of the instant disclosure by disclosure of the specification. The instant disclosure may be implemented or applied by other different specific examples, and each of the details in the specification may be applied based on different views and may be modified and changed under the existence of the spirit of the instant disclosure. The figures in the instant disclosure are only for brief description, but they are not depicted according to actual size and do not reflect the actual size of the relevant structure. The following embodiments further illustrate related technologies of the instant disclosure in detail, but the scope of the instant disclosure is not limited herein.

Unless otherwise specified, the experiment methods used in the following embodiments are all conventional methods.

Unless otherwise specified, the materials, reagents, etc used in the following embodiments could all be obtained commercially.

High fidelity polymerase KAPA HiFi™ HotStar was purchased from Beijing Microread Genetics Co., Ltd.

Wild type $E.$ $coli$ strain K12 W3110 were purchased from NITE Biological Resource Center, NBRC, Japan.

The plasmid pKOV was purchased from Addgene, and the product number is 25769.

Embodiment 1: Determination of 1,5pentanediamine

A 10 µL sample was added into a 2 mL centrifuge tube containing a 100 µL sodium bicarbonate solution (4.2 g/100 mL), after mixture, a 200 µL acetonitrile solution containing 1% (volume percentage) 2,4dinitoflruorobenzene (DNFB) was added therein and then mixed. The derivatization reaction was conducted for 60 minutes at 60° C. (the reaction time was controlled strictly. The mixture was slightly shook for 30 minutes after the reaction started for a better mixing, and then the derivatization reaction was continued). Removed the mixture and cooled the mixture to a room temperature in dark, added a 1600 µL acetonitrile, performed a vortex mixing for 30 seconds, and took a 15 µL sample for injection after a filtration through an organic membrane.

A mobile phase A was 5.4 g/L potassium dihydrogen phosphate solution (pH 7.2), a mobile phase B was 80% (volume percentage) acetonitrile solution, the mobile phases A and B were pumped in at a volume ratio of 5:95, and flow rate of 1 mL/min, by using a C18 column (ZORBAX Eclipse XDBC18, 4.6*150 mm, Agilent, USA) with a column temperature of 35° C. and a detective wavelength of 360 nm.

A 1,5Pentanediamine hydrochloride (purchased from Sigma) was used as a standard, and it showed a good linear relationship of the 1,5pentanediamine hydrochloride concentration in a range of 15 g/L. The calibration curve was plotted with concentrations of the standards as horizontal axis, while versus the peak areas of the standards as the vertical coordinates, and a regression equation was obtained (X=0.000649*Y+0.0176 (R2=0.9999)).

The concentration of 1,5pentanediamine in the following embodiments were calculated according to the regression equation obtained from the calibration curve, the determined value of the 1,5pentanediamine hydrochloride was converted to the concentration of 1,5pentanediamine accordingly.

Embodiment 2: Sequence optimization of lysine decarboxylase gene cadA and construction of expression vector as well as engineering bacteria (1) Inserting an ORF of an optimized lysine decarboxylase gene cadA behind a T7 promoter and a RBS in an expression vectorpET28a (+). First, according to a recognition sequence feature of a restriction endonuclease Nco I which is behind the RBS in the expression vector pET28a (+), mutating a second codon of the lysine decarboxylase gene cadA to GCA which is the second codon with high frequency of an abundant protein. Second, replacing a subsequent sequence before No. +33 base for a synonymous codon by using rare codons, so as to increase the number of the rare codons in the sequence and then increase a gene expression. RNAfold software (http://rna.tbi.univie.ac.at/cgibin/RNAfold.cgi) was further used to predict a minimal free energy of a RNA secondary structure after replacement of No. −4 to +37 base sequences of the lysine decarboxylase gene cadA with the rare codons. Preferably, mutated sequences with the minimal free energy below −6.00 kcal/mol were selected for an optimization. Another software (Salis et al, Nature biotechnology, 2009, 27(10):946950) was further used to calculate a translation initiation efficiency (calculated from No. −33 to +33 base), and further preferably selected the mutated sequences with translation initiation efficiency over 7000 for the optimization from the mutated sequences with lower minimal free energy. The cadA gene with No. +4 to +33 base sequences optimized were obtained through the above design.

According to the above mentioned optimized design of the primers, by using a genome DNA of a wild type $E.$ $coli$ strain K12 W3110 as a template, a high fidelity polymerase KAPA HiFi™ HotStar, and a P1 and a P2 as primers. The cadA gene was amplified by PCR, and the nucleotide sequence of the gene was shown in ID NO. SEQ 1. The PCR program is: degeneration by heating at 98° C. for 30 seconds, annealing at 65° C. for 15 seconds, extension at 72° C. for 150 seconds, and 26 cycles. A mutation N was introduced by primer P1, and the segment of the modified lysine decarboxylase gene cadA* was thus obtained.

(SEQ ID No. 6)
P1:
5'-CATGCCATGGCAGTNATNGCAATATTNAATCANATGGGNGT-3'
(underlined sequence is Nco I recognition locus)

(SEQ ID No. 7)
P2:
5'-ACGCGTCGACCTCCTTATGAGCAAAAAAGGGAAGTG-3'
(underlined sequence is Sal I recognition locus)

(2) The above mentioned PCR electrophoresis strips were purified after being excised from the gel, and then the DNA segment of the lysine decarboxylase gene cadA* as well as the plasmid pET28a(+) were taken to a doubleenzyme digestion by the Nco I and the Sal I, there was thus obtained the corresponding DNA segment of the lysine decarboxylase gene cadA* as well as the larger segment of the plasmid. The obtained lysine decarboxylase gene cadA* segment and the vector segment after digestion were connected and transformed into a competent E. coli EC135 (Zhang et al, Plos Genetics, 2012, 8 (9): e1002987), a transformant was screened on a LB plate containing 50 mg/L kanamycin, and the transformant containing a recombinant plasmids was obtained. The plasmids were extracted and sequenced, and the positive plasmid was named as pET28acadA*, which was shown in FIG. 1.

(3) A construction of control bacteria 1: as shown in FIG. 1, inserting the lysine decarboxylase gene cadA with its own RBS into the vector pET28a (+) behind T7 promoter to construct the control engineering bacteria, by using a P3 and a P2 as primers, the genome DNA of the wild type E. coli K12 W3110 as a template, and a high fidelity polymerase KAPA HiFi™ HotStar for PCR amplification under the same condition as above.

```
                                          (SEQ ID No. 8)
P3:    5'-TGCTCTAGAACCTGGAGATATGACTATGAACGT-3'
(underlined sequence is Xba I recognition locus)
```

The above mentioned PCR electrophoresis strips were purified after being excised from the gel, and then the excised DNA segment and the plasmid pET28a(+) were taken to a doubleenzyme digestion by the Xba I and the Sal I, there was thus obtained the larger vector segment. The excised gene segment and the larger vector segment after digestion were connected, and the recombinant plasmid named as pET28acadA1 was obtained, which was sequenced and got the positive result.

A construction of control bacteria 2: as shown in FIG. 1, the second codon of cadA gene was experienced deletion, so that the fourth base position was as the recognition locus of Nco I, and a vector overexpressing cadA was constructed. A P4 and a P2 were used as primers for PCR amplification. The above mentioned PCR electrophoresis strips were purified after being excised from the gel, and then the excised DNA segment and the plasmid pET28a(+) were taken to the doubleenzyme digestion by the Nco I and the Sal I, there was thus obtained the larger vector segment. The excised gene segment and the larger vector segment after digestion were connected and transformed into the competent E. coli EC135, then the transformant was screened on the LB plate containing 50 mg/L kanamycin, and the transformant containing the recombinant plasmids was obtained. The plasmids were extracted and sequenced, and the positive plasmid was named as pET28acadA2.

```
                                          (SEQ ID No. 9)
P4:    5'-CATGCCATGGTTATTGCAATATTGAATCACATGGGGGT-3'
```

The above mentioned plasmids pET28acadA*, pET28acadA1 and pET28acadA2 were transformed into the competent E. coli BL21 (DE3) cells, then screened on the LB plate containing 50 mg/L kanamycin. The engineering bacteria E. coli BL21 (DE3)/pET28acadA1, E. coli BL21 (DE3)/pET28acadA2 and the E. coli BL21 (DE3)/pET28acadA* were obtained, and the catalytic performance of the 1,5pentanediamine in the engineering bacteria were further verified by shaking flask.

Embodiment 3: Screening the whole cell catalytic performance of E. coli BL21 (DE3)/pET28acadA*

The above constructed engineering bacteria E. coli BL21 (DE3)/pET28acadA* as well as the control engineering bacteria E. coli BL21 (DE3)/pET28acadA1 and the E. coli BL21 (DE3)/pET28acadA2 stored in freezing tube at −80° C. were inoculated by streaking respectively on the LB culture plates containing 50 mg/L kanamycin, and incubated in the culture incubator at 37° C. for 12 h. The lawn on the culture plate were removed and inoculated in another tube containing 3 mL LB liquid culture media (with 50 mg/L kanamycin), and cultured in the shaking incubator at 37° C. with 200 rpm for 10 h. A 2% (volume ratio) bacteria solution was taken and inoculated into a 500 mL shaking flask with 50 mL LB liquid medium (containing 50 mg/L kanamycin), and cultured in the shaking incubator at 37° C. with 200 rpm. An inducer IPTG at a final concentration of 0.2 mM was added after 2.5 h incubation, and an inducing culture was conducted for 2 h under the same condition in the shaking incubator. The light absorption $OD_{600}$ was determined and used to calculate a cell dry weight by multiplying 0.42. An aqueous solution in an equal volume containing 400 g/L commercial feeding lysine hydrochloride (98.5% purity) and 0.1 g/L pyridoxal phosphate was added. The whole cell catalysis was performed under the same condition in the shaking incubator for 1 h, and centrifuged after sampling. The supernatant was taken and stored in −20° C. for a 1,5pentanediamine concentration determination, and the determination method was described in embodiment 1.

By using a shake flask catalytic screening, the specific production rate of 1,5pentanediamine per unit cell quantity, namely specific production rate, was calculated as: specific production rate=1,5pentanediamine production per hour/cell dry weight. A plurality of engineering bacteria with improved catalytic performance were obtained, as shown in Table 1, in which the specific production rate of engineering bacteria 51#, 55# and 59# were 33.94±1.96 g/g/h, 33.31±3.23 g/g/h and 31.21±1.42 g/g/h, respectively, which were significantly higher than that of control bacteria strains. Table 1. Comparation of the catalytic performance of the engineering bacteria in the whole cell catalysis of 1,5pentanediamine.

The corresponding P1 primer sequences of the engineering bacteria 50#, 51#, 53#, 55#, 48#, 57#, 58# and 59# (see embodiment 2) are as follows:

```
                                         (SEQ ID No. 10)
P1-48:  5-CATGCCATGGCAGTTATAGCAATATTGAATCATATGGGAGT (SEQ ID No. 11)
P1-50:  5-CATGCCATGGCAGTTATAGCAATATTGAATCACATGGGGGT (SEQ ID No. 12)
P1-51:  5-CATGCCATGGCAGTTATAGCAATATTAAATCACATGGGGGT (SEQ ID No. 13)
P1-53:  5-CATGCCATGGCAGTTATTGCAATATTGAATCACATGGGAGT
```

| Engineering bacteria | Specific production rate of 1,5-pentanediamine G/g/h |
|---|---|
| Control bacteria 1 | 0.74 ± 0.06 |
| Control bacteria 2 | 9.59 ± 0.13 |
| Engineering bacteria 48# | 23.84 ± 2.10 |
| Engineering bacteria 50# | 27.36 ± 1.17 |

-continued

| Engineering bacteria | Specific production rate of 1,5-pentanediamine G/g/h |
|---|---|
| Engineering bacteria 51[#] | 33.94 ± 1.96 |
| Engineering bacteria 53[#] | 24.90 ± 2.73 |
| Engineering bacteria 55[#] | 33.31 ± 3.23 |
| Engineering bacteria 57[#] | 24.84 ± 1.40 |
| Engineering bacteria 58[#] | 23.08 ± 2.24 |
| Engineering bacteria 59[#] | 31.21 ± 1.42 |

(SEQ ID No. 14)
P1-55: 5-CATG<u>CCATGG</u>CAGTTATTGCAATATTGAATCATATGGGAGT (SEQ ID No. 15)
P1-57: 5-CATG<u>CCATGG</u>CAGTTATTGCAATATTGAATCACATGGGGT (SEQ ID No. 16)
P1-58: 5-CATG<u>CCATGG</u>CAGTTATTGCAATATTAAATCACATGGGGT (SEQ ID No. 17)
P1-59: 5-CATG<u>CCATGG</u>CAGTTATTGCAATATTAAATCATATGGGAGT

Embodiment 4: Expression optimization of lysinecadaverine antiporter gene cadB

1. Obtaining E. coli BL21 (DE3)/pET28acadA*[55]

By using a P155 and a P2 as primers for PCR amplification, pET28acadA*[55] was constructed according to the method described in embodiment 2(1), the plasmid was transformed into the competent E. coli BL21 (DE3), and there was thus obtained the engineering bacteria E. coli BL21 (DE3)/pET28acadA*[55] which abbreviated as engineering bacteria pA.

2. Obtaining E. coli BL21 (DE3)/pET28acadBA (1) By using the genome DNA of the wild type E. coli strain K12 W3110 as a template, a high fidelity polymerase KAPA HiFi™ HotStar, a P5 and a P6 as primers for the PCR amplification, and the PCR program that is: degeneration by heating at 98° C. for 30 seconds, annealing at 65° C. for 15 seconds, extension at 72° C. for 150 seconds, and 26 cycles the 3604 bp cadBA segment (cadB and cadA genes are both on the same operon cadBA, therefore the product segment contains the products of the above two genes) was obtained, which in the nucleotide sequence of cadB gene is shown in SEQ ID No.2.

(SEQ ID No. 18)
P5: 5'-CATG<u>CCATGG</u>GTTCTGCCAAGAAGATCGGGCT-3'
(underlined sequence is Nco I recognition locus)

(SEQ ID No. 19)
P6: 5'-CCC<u>AAGCTT</u>GCAAGCCACTTCCCTTGTACGAGCTA-3'
(underlined sequence is Hind III recognition locus)

(2) The above mentioned DNA molecules obtained by PCR were taken to a doubleenzyme digestion by the Nco I and the Hind III, and there was thus obtained the corresponding gene segment. The pET28a(+) was taken to the doubleenzyme digestion by the Nco I and the Hind III, and there was thus obtained the larger vector segment. The gene segment and the larger vector segment after digestion were connected and transformed into the competent E. coli EC135, then the transformant was screened on the LB plate containing 50 mg/L kanamycin, and the transformant containing the recombinant plasmids was obtained. The plasmids were extracted and sequenced, and the positive plasmid was named as pET28acadBA.

(3) The recombinant plasmid pET28acadBA was transformed into the competent E. coli BL21 (DE3) cells, and screened on the LB plate containing 50 mg/L kanamycin. The engineering bacteria E. coli BL21 (DE3)/pET28acadB was obtained, which abbreviated as engineering bacteria pBA.

2. Obtaining E. coli BL21 (DE3)/pET28acadA*[55]RBS$_{native}$cadB (1) By using the genome DNA of the wild type E. coli strain K12 W3110 as a template, a high fidelity polymerase KAPA HiFi™ HotStar, a P7 and a P9 as primers for the PCR amplification, and the PCR program that is: degeneration by heating at 98° C. for 30 seconds, annealing at 65° C. for 15 seconds, extension at 72° C. for 150 seconds, and 26 cycles, the lysinecadaverine antiporter gene sequence with its own RBS, RBS$_{native}$cadB was obtained.

(SEQ ID No. 20)
p7: 5'-CCC<u>AAGCTTT</u>GAAATTAGGAGAAGAGCATG-3'
(underlined sequence is Hind III recognition locus)

(SEQ ID No. 21)
P8: 5'-CCC<u>AAGCTT</u>CTAGGAAGTAGAGCATGAGTTCTGCCAAGA-3'
(underlined sequence is Hind III recognition locus)

(SEQ ID No. 22)
P9: 5'-ATAAGAAT<u>GCGGCCGC</u>TTAATGTGCGTTAGACGCGGT-3'
(underlined sequence is Not I recognition locus)

(2) The above mentioned DNA molecules obtained by PCR were taken to the doubleenzyme digestion by the Not I and the Hind III, and there was thus obtained the corresponding gene segment. The pET28acadA*[55] was taken to the doubleenzyme digestion by the Not I and the Hind III, and there was thus obtained the larger vector segment. The gene segment and the larger vector segment after digestion were connected and transformed into the competent E. coli EC135. The transformant was screened on the LB plate containing 50 mg/L kanamycin, and the transformant containing the recombinant plasmids was obtained. The plasmids were extracted and sequenced, and the positive plasmid was named as pET28acadA*[55]RBS$_{native}$-cadB.

(3) The pET28acadA*[55]RBS$_{native}$cadB was transformed into the competent E. coli BL21 (DE3) cells, and screened on the LB plate containing 50 mg/L kanamycin. The engineering bacteria E. coli BL21 (DE3)/pET28acadA*[55]RBS$_{native}$cadB was obtained, which abbreviated as engineering bacteria pAB.

3. Obtaining E. coli BL21 (DE3)/pET28acadA*[55]RBS$_{BCD22}$cadB (1) By using the genome DNA of the wild type E. coli strain K12 W3110 as a template, a high fidelity polymerase KAPA HiFi™ HotStar, a P8 and a P9 as primers for the PCR amplification, and the PCR program that is: degeneration by heating at 98° C. for 30 seconds, annealing at 65° C. for 15 seconds, extension at 72° C. for 150 seconds, and 26 cycles, the lysinecadaverine antiporter gene sequence containing weak RBS (Mutalik et al, Nature methods, 2013. 10(4): 354360.) RBS$_{BCD22}$cadB was obtained, and the nucleotide sequence of the RBS$_{BCD22}$ segment is shown in SEQ ID No.3.

(2) The above mentioned DNA molecules obtained by PCR were taken to the doubleenzyme digestion by the Not I and the Hind III, and there was thus obtained the corresponding gene segment. The pET28acadA*[55] was taken to the doubleenzyme digestion by the Not I and the Hind III, and there was thus obtained the larger vector segment. The gene segment and the larger vector segment after digestion were connected and transformed into the competent E. coli EC135. The transformant was screened on the LB plate containing 50 mg/L kanamycin, and the transformant containing the recombinant plasmids was obtained. The plasmids were extracted and sequenced, and the positive plasmid was named as pET28acadA*$^{55}$RBS$_{BCD22}$CadB.

(3) The pET28acadA*$^{55}$RBS$_{BCD22}$cadB was transformed into the competent E. coli BL21 (DE3) cells, and screened on the LB plate containing 50 mg/L kanamycin. The engineering bacteria E. coli BL21 (DE3)/pET28acadA*$^{55}$RBS$_{BCD22}$cadB was, which abbreviated as engineering bacteria pARBS$_{BCD22}$B.

4. Replacing the promoter of cadB gene on the chromosome of E. coli (1) By using the genome DNA of the E. coli strain BL21(DE3) as a template, a P10/P11 and a P12/P13 as primers respectively for the PCR amplification, two DNA segments of 510 bp and 610 bp were obtained, as shown in SEQ ID No.4 and SEQ ID No.5, respectively. A T7 promoter sequence and a lac sequence were introduced by the P9 and the P10 primers. The PCR program is: degeneration by heating at 94° C. for 30 seconds, annealing at 52° C. for 30 seconds, extension at 72° C. for 30 seconds (30 cycles). In addition, the primer sequences list as follows:

```
p10:
                                      (SEQ ID No. 23)
5'-CGCGGATCCTGCGCCATTCTCAACATCCTT-3'
(underlined sequence is BamHI recognition locus)

P11:
                                      (SEQ ID No. 24)
5'-TCCGCTCACAATTCCCCTATAGTGAGTCGTATTATGCCGCA

ACATATT ATACCAACAG-3'

P12:
                                      (SEQ ID No. 25)
5'-ACTCACTATAGGGGAATTGTGAGCGGATAACAATTCCGAAATTAG

GAGAAGAGCATGAG-3'

P13:
                                      (SEQ ID No. 26)
5'-ATTGCGGCCGC TCCGCAGTATTCCAGTTAGCT-3'
(underlined sequence is Not I recognition locus)
```

(2) By using the DNA segments as shown in SEQ ID No.4 and SEQ ID No.5 as templates, a P10 and a P13 as primers, about 1.1 kb amplified overlap segment was obtained by overlap extension PCR, as shown in SEQ ID No.29. The PCR program is: degeneration by heating at 94° C. for 30 seconds, annealing at 52° C. for 30 seconds, extension at 72° C. for 60 seconds, and 26 cycles.

No. 477495 nucleotide sequence of 5' end in SEQ ID No.29 is the T7 promoter sequence, and No. 496520 nucleotide sequence of 5' end in SEQ ID No.29 is the lac regulatory sequence.

The gene segment was obtained from DNA molecule shown in SEQ ID No.29 after the doubleenzyme digestion by a Bam HI and a Not I. The larger segment of vector was obtained from the plasmid pKOV after the doubleenzyme digestion by the Bam HI and the Not I. The gene segment and the larger segment of vector were connected to obtain the recombinant plasmid, which was named as pKOVP$_{T7}$cadB, and the recombinant plasmid was stored. It contained the correct T7 promoter and lac regulatory gene sequence, which was verified by sequencing.

(3) The constructed plasmid pKOVP$_{T7}$cadB was electronically transformed into the E. coli strain BL21 (DE3), and recovered in LB medium at 30° C. for 2 h with 150 rpm. According to the protocol of the plasmid pKOV provided by Addgene, picked up the positive monoclone of the homologous recombination, the promoter of cadB gene on the chromosome was replaced with the T7 promoter and identified through sequencing, and the strain was named as E. coli BL21 P$_{cadB}$:: P$_{T7}$. The plasmid pET28acadA*$^{55}$ was further transformed into the strain, and the engineering bacteria E. coli BL21 P$_{cadB}$:: P$_{T7}$/pET28acadA*$^{55}$ was obtained, abbreviated as ChrT7B.

Example 5: Identifying the induced expression of cadB by reverse transcription PCR According to the culture and inducing methods of E. coli in embodiment 3, the engineering bacteria pA and ChrT7B were collected 2 h after inducement. RNA was isolated and the induced expression of cadB was identified by a reverse transcription PCR Total RNA isolation kit for bacteria (TIANGEN Biotech Co., Ltd.), and the detail steps for total RNA isolation according to the protocol are as follows: collecting fresh cultured bacteria cells to dilute, till an OD$_{600}$ value is approximately 0.8, taking out 1 mL dilution to centrifuge at 13,400×g for 2 minutes at 4° C., and resuspending with deionized water to centrifuge for 2 min. Resuspending bacteria thoroughly with 100 µL TE buffer containing 0.40 mg/mL lysozyme, and incubating for 8 min. 350 µL lysis buffer RL was added and mixed by a vortex, and was centrifuged at 13,400×g for 2 min if an insoluble precipitate had been formed. The supernatant was then transferred to another centrifuge tube. 250 µL ethanol was added therein and mixed. The obtained supernatant and precipitation were transferred together into an spin column CR3 which was placed in a collection tube, centrifuged at 13,400×g for 1 minutes, and then placed the column back in the original collection tube after the supernatant was removed. 350 µL protein cleanup buffer RW1 was added into the spin column CR3, centrifuged at 13,400×g for 1 min, and then placed the column back in the original collection tube after the supernatant was removed. 80 µL DNase I buffer was added into the spin column CR3, and placed at room temperature for 30 min. Next, the 350 µL protein cleanup solution RW1 was added into the spin column CR3, centrifuged at 13,400×g for 1 min, and then placed the column CR3 back in the original collection tube after the supernatant was removed. 500 µL rinse buffer RW was added into the spin column CR3, and placed at room temperature for 2 min, centrifuged at 13,400×g for 1 min, and then placed the column back in the original collection tube after the supernatant was removed. Repeated rinsing once, centrifuged at 13,400×g for 2 min, removed the supernatant, and the spin column CR3 was placed at room temperature for 8 min to completely dry the residual of rinse buffer in the column fillings. The spin column CR3 was transferred into a new RNaseFree centrifugal tube, 60 µL RNaseFree ddH$_2$O was dropped directly to the center of the column membrane, placed at room temperature for 2 min, and centrifuged at 13,400×g for 2 min to obtain a RNA solution. 1.5 µg total RNA was added into 2 µL loading buffer, and detected by gel electrophoresis. The isolated RNA after detection qualified was stored at −80° C.

A FastQuant cDNA first strand synthesis kit (TIANGEN Biotech Co., Ltd.) was used, and a template RNA was thawed on ice. 5×gDNA buffer, FQRT primer Mix, 10×Fast RT buffer, and RNaseFree ddH$_2$O were thawed at room temperature, and placed on ice immediately after thawing. Each solution was mixed by the vortex, and centrifuged briefly to collect residual liquid from the sides of the tubes. The mixture was prepared according to the reaction system for cleanup gDNA in Table 2, mixed thoroughly, centrifuged briefly, placed at 42° C., incubated for 30 min, and then placed on ice.

TABLE 2

Reaction system for clean-up gDNA

| Components | Amount |
|---|---|
| 5 × gDNA buffer | 2.00 μL |
| Total RNA | 0.25 μg RNA |
| RNase-Free ddH$_2$O | add up to 10.00 μL |

Prepared reversetranscription reaction system in accordance with the same reaction system (10.00 μL), as shown in below Table 3.

TABLE 3

Reaction system for reverse-transcription

| Components | Amount |
|---|---|
| 10 × Fast RT buffer | 2.00 μL |
| RT Enzyme Mix | 1.00 μL |
| FQ-RT primer Mix (reverse primer) | 2.00 μL |
| RNase-Free ddH$_2$O | Up to 10.00 μL |

The RT Enzyme Mix in reverse transcription system was added into the reaction system for cleanup gDNA, mixed thoroughly, incubated at 42° C. for 30 min, heated to 95° C. and maintained for 5 min, and then placed on ice. The cDNA was obtained and stored at −20° C. The reverse primer was P14 and the forward primer was P15 shown as follows:

```
P14:  5'-TACCGTTGCTGTCGACTTCA-3'   (SEQ ID No. 27)

P15:  5'-CTCCGTTTGCAATCAGTGCT-3'   (SEQ ID No. 28)
```

Figure 3:
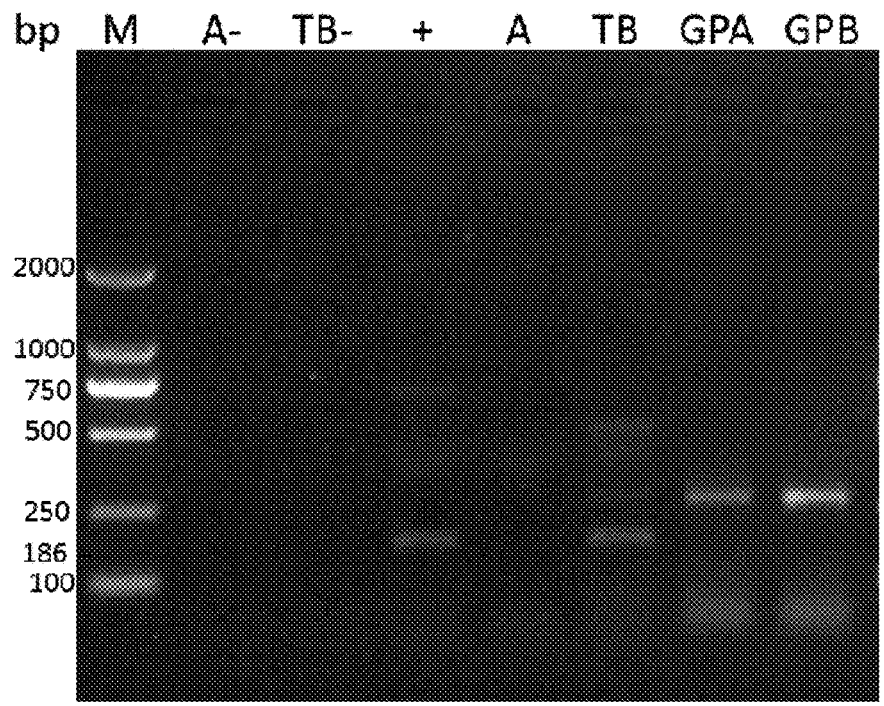
FIG. 3 is a reverse transcriptionPCR electrophoresis gel of gene cadB.

The induced engineering bacteria *E. coli* pA and *E. coli* ChrT7B cDNA were used as templates, a BL21 chromosome genome was used as a positive control template (+), a RNA of which the gDNA removed before reverse transcription were used as negative control templates (A− and TB−), a gapA gene was used as reference genes (GPA and GPB), a P14 and a P15 were used as primers, and a Taq DNA polymerase was used for PCR amplification. As the nucleic acid electrophoretogram of PCR products (FIG. 3) shown, the target strip could be observed in the lanes of reference genes GPA and GPB, which indicated a successful reverse transcription. While the target strip could not be amplified from the cDNA of negative control (A− and TB−) or engineering bacteria pA (A), however the target strip (186 bp) could be amplified from the cDNA of positive control (+) and engineering bacteria ChrT7B, which indicated a successful expression of induced cadB gene in the engineering bacteria ChrT7B.

Figure 2:
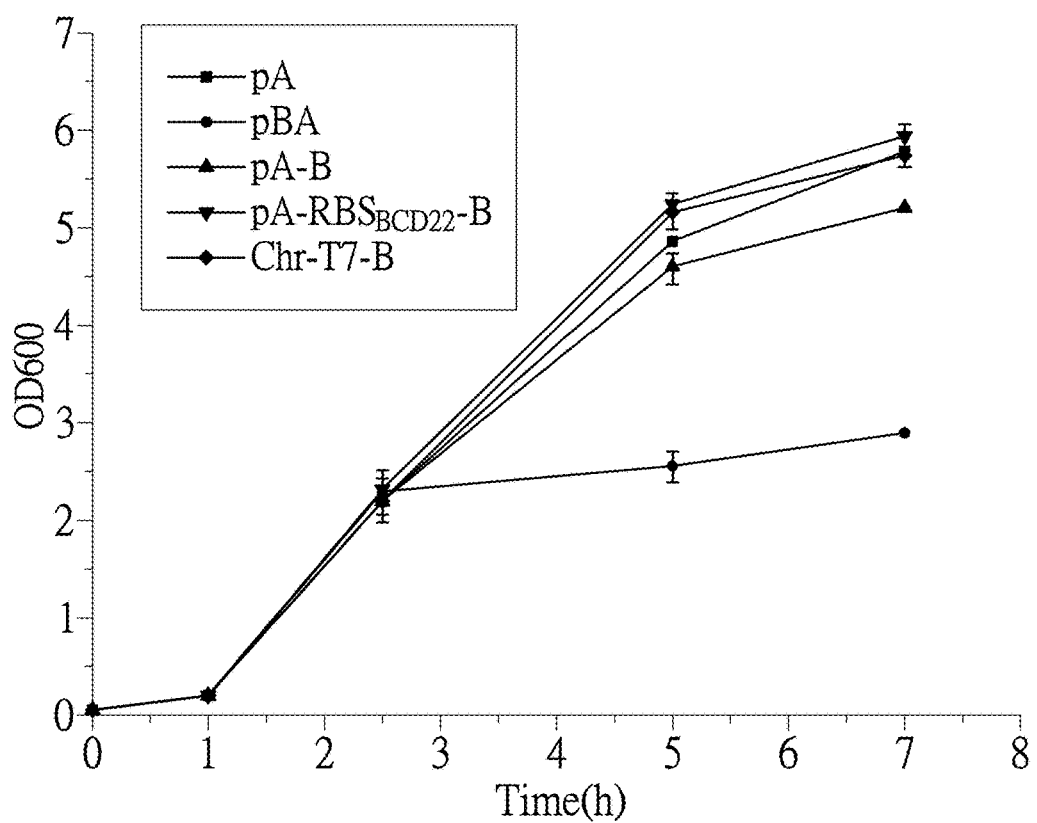
FIG. 2 is a cultivation profile of engineering bacteria with different overexpression combination of a cad operon gene.

Embodiment 6: Influences of the induced expression of lysinecadaverine antiporter gene cadB on the growth of the engineering bacteria as well as on the catalysis of pentanediamine The engineering bacteria *E. coli* BL21 (DE3)/pET28acadA*$^{55}$ (abbreviated as pA in FIG. 2), *E. coli* BL21 (DE3)/pET28acadBA (abbreviated as pBA in FIG. 2), *E. coli* BL21 (DE3)/pET28acadA*$^{55}$RBS$_{native}$cadB (abbreviated as pAB in FIG. 2), *E. coli* BL21 (DE3)/pET28acadA*$^{55}$RBS$_{BCD22}$cadB (abbreviated as pARBS$_{BCD22}$B in FIG. 2), as well as *E. coli* BL21 (DE3) P$_{cadB}$:: PT7/pET28acadA*$^{55}$ (abbreviated as ChrT7B in FIG. 2) stored in freezing tubes at −80° C. were inoculated by streaking respectively on the LB culture plates containing 50 mg/L kanamycin, incubated in the culture incubator at 37° C. for 12 h, the lawn on the culture plate were removed and to inoculate in another tube containing 3 mL LB liquid culture media (with 50 mg/L kanamycin), and cultured in the shaking incubator at 37° C. with 200 rpm for 10 h. The 3% (volume ratio) bacteria solution was taken and inoculated into a 500 mL shaking flask with 50 mL LB liquid medium (containing 50 mg/L kanamycin), and cultured in the shaking incubator at 37° C. with 200 rpm. The light absorption at 600 nm (OD$_{600}$) was determined after sampling every 2 h. After 2.5 h, the inducer IPTG was added therein with a final concentration of 0.2 mM, the growth curve of the induced bacteria cells was shown in FIG. 2. After the inducer was added, the engineering bacteria pBA whose plasmids containing overexpressed cadBA operon according to the original gene sequence was almost stopped growing. While the engineering bacteria pAB and pARBS$_{BCD22}$B whose plasmids containing genes with rearranged sequence, as well as the engineering bacteria whose chromosomes were integrated with a strong promoter T7, that could continue growing, which is little difference from the control bacteria pA. It was further found that the growth rate of the engineered bacteria with induced expression of cadB could be increased, by overexpression of cadB gene using weak RBS$_{BCD22}$ on the plasmids or strong replacing promoter on the chromosomes.

According to the method in Embodiment 3, the catalytic performance of the engineering bacteria was compared through shaking flask whole cell catalysis. The catalytic performance in producing the pentanediamine of the engineering bacteria ChrT7B was the highest, which was increased by 13.9% compared with the control engineering bacteria pA.

Embodiment 7: Inducing the expression of target protein with different inducers, IPTG or lactose The engineering bacteria *E. coli* BL21 (DE3)/pET28acadA2RBS$_{BCD22}$cadB stored in freezing tube at −80° C. was inoculated by streaking respectively on the LB culture plates containing 50 mg/L kanamycin, and incubated in the culture incubator at 37° C. for 12 h. The lawn on the culture plate were removed and to inoculate in another tube containing 3 mL LB liquid culture media (with 50 mg/L kanamycin), and cultured in the shaking incubator at 37° C. with 200 rpm for 10 h. The 3% (volume ratio) bacteria solution was taken and inoculated into a 500 mL shaking flask with 50 mL LB liquid medium (containing 50 mg/L kanamycin), and cultured in the shaking incubator at 37° C. with 200 rpm. The inducer IPTG at a final concentration of 0.1 mM, as well as 2 mM and 100 mM lactose were added after 3.5 h incubation, and then cultured for 4 h. The culture media with and without adding the inducer were centrifuged, the bacteria cells were resuspended in 0.05M TrisHCl buffer (pH7.5), and there was thus obtained the suspension by adjusting OD$_{600}$=4.0. 16 μL suspensions were added into 6 μL 5× Loading Buffer respectively, and treated at 95° C. for 10 minutes. 5 μL samples after treatments were taken to SDSPAGE, and the electrophoresis results after staining and destaining were shown in FIG. 4.

Figure 4:
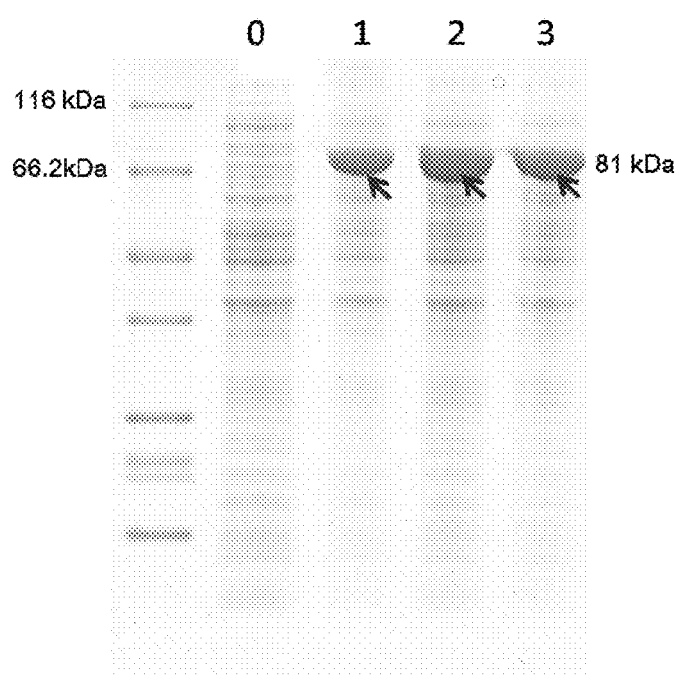
FIG. 4 is a PAGE gel (protein electrophoresis) of a cadA gene expression protein induced by an IPTG and a lactose.
Figure 5:
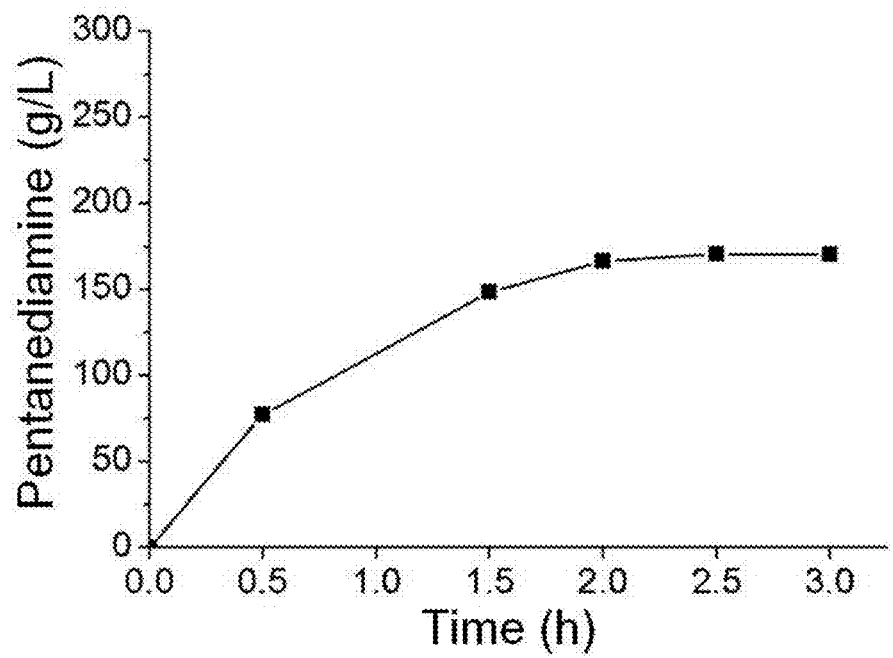
FIG. 5 is a 1,5pentanediamine production yield through a whole cell catalysis with a substrate lysine hydrochloride concentration at 300 g/L.
Figure 6:
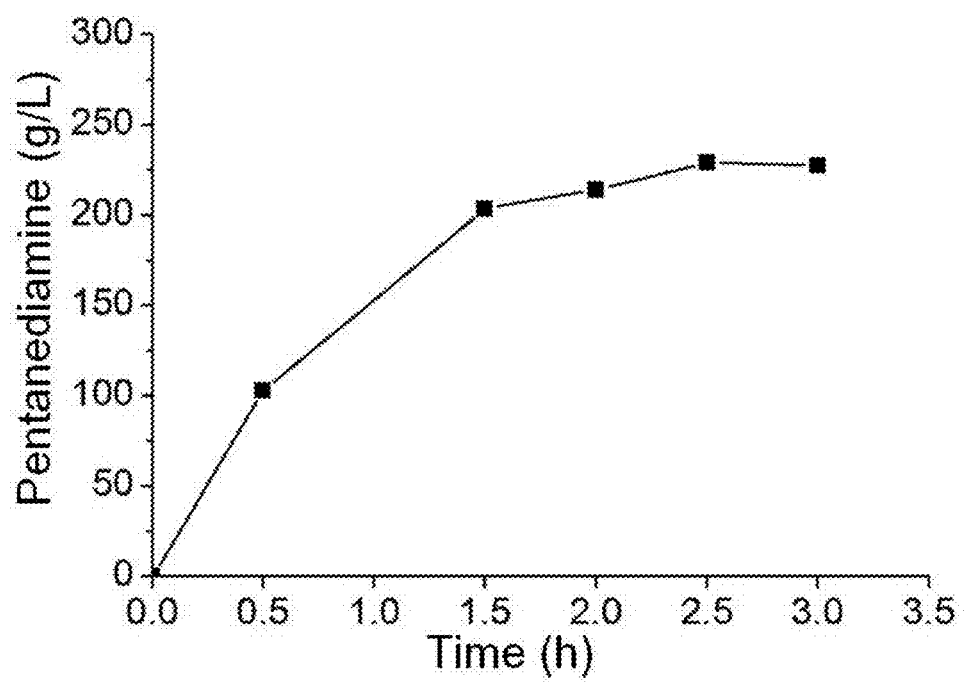
FIG. 6 is a 1,5pentanediamine production yield through a whole cell catalysis with a substrate lysine hydrochloride concentration at 400 g/L.
Figure 7:
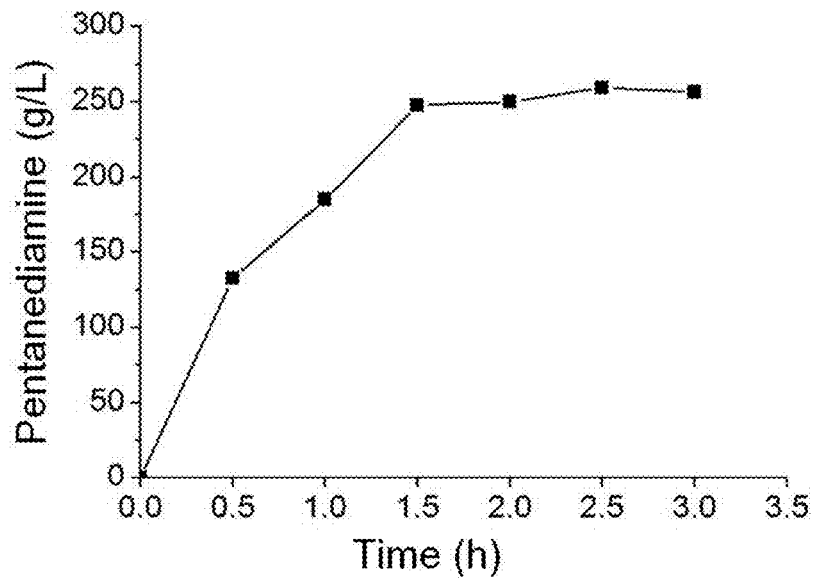
FIG. 7 is a 1,5pentanediamine production yield through a whole cell catalysis with a substrate lysine hydrochloride concentration at 450 g/L.
Figure 8:
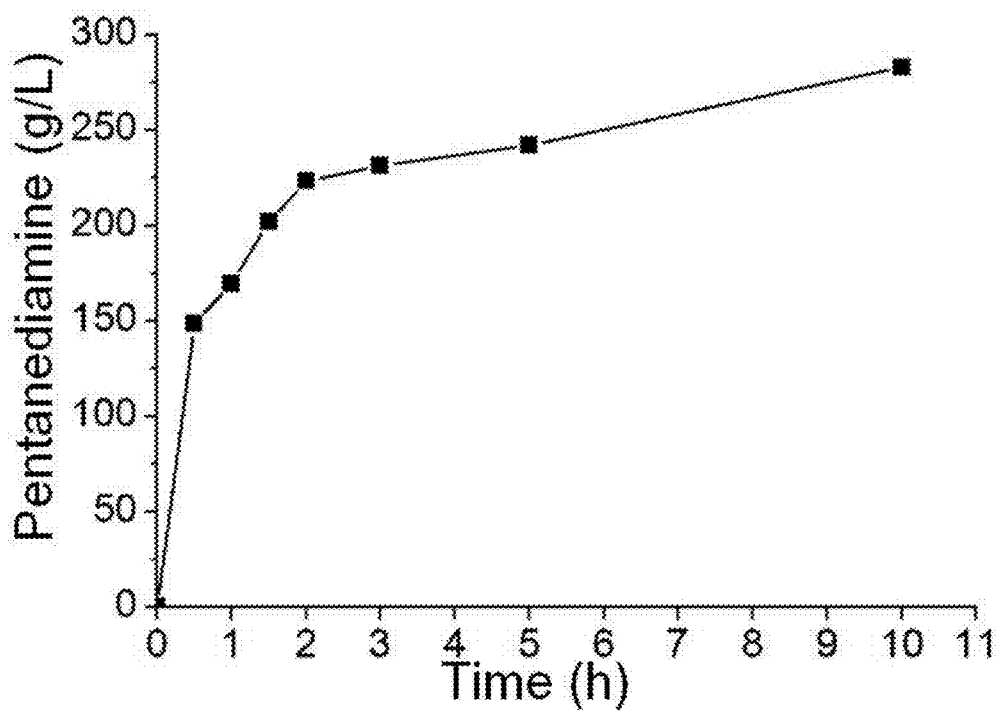
FIG. 8 is a 1,5pentanediamine production yield through a whole cell catalysis with a substrate lysine hydrochloride concentration at 500 g/L.

As FIG. 4 shows, compared with Lane No. 0 which is the control without adding the inducer, the strips of 81 kD target protein (protein CadA) were all observed in Lane No. 1 with adding 0.1 mM IPTG Lane No. 2 with adding 2 mM lactose, and Lane No. 3 with adding 100 mM lactose, which indicated that both IPTG and lactose could induce the expression of target protein successfully.

Embodiment 8: Bacteria culturing in rich medium and continuous producing technology of 1,5pentanediamine by catalysis The lawn of the engineering bacteria E. coli BL21 (DE3) $P_{cadB}$:: PT7/pET28acadA*$^{55}$ (abbreviated as ChrT7B) was removed and inoculated into a 500 mL conical flask containing 50 mL LB culture media (with 50 mg/L kanamycin, the kanamycin concentration could be in a range of 5200 mg/L), cultured in the shaking incubator at 37° C. with 200 rpm for 4 h, and there was thus obtained the seed solution whose $OD_{600}$ value was in a range of 45. The cultured seed solution was inoculated into a 7.5 L fermentor containing 2 L rich medium. The culture temperature was 37° C., the DO was controlled to above 50%, the pH value was in a range of 4.09.0, and the fermentor was pressurized or supplied with pure oxygen if necessary. 0.4 mM IPTG was added to induce expression for 3 h, and fed with glucose at the rate of 3 g/L. The $OD_{600}$ value was 25.1 after culturing for 6 h, 300 g/L Llysine hydrochloride and 0.08 g/L pyridoxal phosphate were added therein, and the whole cell catalysis was started. The pH value was increased rapidly in the catalytic process, thus the additional sulphuric acid was fed to maintain the pH value at 6.5. In the catalytic process, the aeration rate was 1 vvm, the temperature was controlled at 37° C., and the stirrer speed was 500 rpm.

The rich medium contains: 10 g/L yeast extract, 20 g/L peptone, 0.9 g/L $K_2HPO_4.3H_2O$, 1.14 g/L $KH_2PO_4$, 10 g/L $(NH_4)_2SO_4$, 0.3 g/L $MgSO_4.7H_2O$, 5 mL/L trace elements stock solution, 50 mg/L kanamycin, and water for the rest.

The trace elements stock solution contains 6 g/L $FeSO_4.7H_2O$, 1.35 g/L $CaCl_2$, 0.8 g/L $ZnSO_4.7H_2O$, 1.5 g/L $MnSO_4.4H_2O$, 0.15 g/L $CuSO_4.5H_2O$, 0.2 g/L $(NH_4)_6Mo_7O_{24}.4H_2O$, 0.1 g/L $H_3BO_3$, 0.25 g/L $CoCl_2.6H_2O$, 10 mL/L HCL (concentrated), and water for the rest.

2 mL catalytic products were taken out of the fermentor at 0.5, 1.0 and 1.5 h during the catalysis process, and were centrifuged at 12,000×g for 5 min. The supernatant was taken out and detected for the 1,5pentanediamine content. The production yield of 1,5pentanediamine during whole cell catalysis process was determined according to the method in Embodiment 1. As the results shown in Table 4, 151.5 g/L (1.48 mol/L) 1,5pentanediamine could be produced catalytically in 1.5 h by the engineering bacteria using the present producing technology.

TABLE 4

Production yield of 1,5-pentanediamine with different catalytic time

| Catalysis reaction time (h) | 1,5-Pentanediamine concentration (g/L) |
| --- | --- |
| 0.5 | 75.1 |
| 1.0 | 115.2 |
| 1.5 | 151.5 |

Embodiment 9: Bacteria culture by using minimal medium and producing technology of 1,5pentanediamine catalysis The culturing conditions for the seed solution were the same as in Embodiment 6, 2% of the cultured seed solution was inoculated into a 7.5 L fermentor containing 2 L minimal medium, the culture temperature was 37° C., the DO was controlled to above 50%, and the fermentor was pressurized or supplied with pure oxygen if necessary. The concentration of glucose in the culture medium was maintained below 5 g/L by fedbatch. When the $OD_{600}$ value of the bacteria cells reached 4050 after cultured for about 7 h, 0.1 mM inducer IPTG were added therein, and the $OD_{600}$ value of the bacteria cell solution increased to above 80 after 2 h. The wet cells were obtained by centrifuge, 20 g wet cells were weighed and added into 2 L (volume including roughly that of the bacteria cell feeding suspension and phosphate reserved) whole cell catalytic solution systems containing 600 g, 800 g, 900 g or 1000 g lysine hydrochloride as well as 0.16 g pyridoxal phosphate, and then the production of 1,5pentanediamine by catalysis was started. In the catalytic process, an additional phosphoric acid was fed to maintain the pH value at 6.5, the aeration rate was 1 vvm, the temperature was controlled at 37° C., and the stirrer speed was 500 rpm.

In addition, the components of the minimal medium and the fed solution were as follows:

Minimal medium: 2 g/L $(NH_4)_2HPO_4$, 4 g/L $KH_2PO_4$, 0.85 g/L citric acid, 0.7 g/L $MgSO_4.7H_2O$, 10 mg/L $FeSO_4.7H_2O$, 2.25 mg/L $ZnSO_4.7H_2O$, 0.2 mg/L $CuSO_4.5H_2O$, 0.5 mg/L $MnSO_4.5H_2O$, 0.23 mg/L $NaB_4O_7.10H_2O$, 2.0 mg/L $CaCl_2.2H_2O$, 0.1 mg/L $NH_4Mo_7O_{24}$, 0.15 mg/L $CoCl_2.6H_2O$, and water for the rest.

The fed solution containing 700 g/L glucose and 20 g/L $MgSO_4.7H_2O$, and water for the rest.

The catalytic solutions were taken out of the fermentor every 0.5 h, and centrifuged at 12,000×g for 5 min. The supernatant was taken out and detected for the 1,5pentanediamine content. The production yield of 1,5pentanediamine during the whole cell catalysis process was determined according to the method in Embodiment 1. As the results shown in FIGS. 5 to 8, the final yield of the pentanediamine increased with the increasing concentration of the substrate lysine hydrochloride, when the substrate concentration was 500 g/L, the yield of the pentanediamine could reach 282.85 g/L after 10 h catalysis. While when the substrate concentration were 300450 g/L, the maximal yields of the pentanediamine were reached at 2.5 h in all batches catalysis, which were 170.49 g/L, 229.08 g/L and 256.60 g/L respectively. During the first 0.5 h in the pentanediamine producing process through the whole cell catalysis, when 300 g/L, 400 g/L, 450 g/L and 500 g/L substrate lysine hydrochloride were added, the corresponding production rate (production intensity) could reach 154.50 g/L/h, 206.01 g/L/h, 265.04 g/L/h and 296.97 g/L/h respectively, while the total production intensity were 68.20 g/L/h, 91.63 g/L/h, 102.64 g/L/h and 28.29 g/L/h respectively.

In summary, the beneficial effects of the instant disclosure are, in the instant disclosure, the E. coli engineering bacteria producing the 1,5pentanediamine through the whole cell catalysis is constructed starting from an E. coli strain B, which is suitable for a high efficient protein expression. By an overexpression of a lysine decarboxylase gene and a proper expression of a lysinecadaverine antiporter gene cadB in the E. coli strain B or its derivative strains, the inhibition problem of bacterial growth in the prior art is solved, and a catalytic performance of the 1,5pentanediamine is improved significantly. The instant disclosure further provides a method for producing the 1,5pentanediamine by using the engineering bacteria through the whole cell catalysis, a production yield of the 1,5pentanediamine could be in a range of 100300 g/L, and a production intensity of the 1,5pentanediamine could be in a range of 50300 g/L/h, which realized a 1,5pentanediamine production through the catalysis with a high production intensity and a high yield. Compared with the prior arts, the production yield and production rate of the pentanediamine are increased many times by using the technology in the instant disclosure. The cost for producing the 1,5pentanediaminein is reduced, thus it could be applied to mass production of the 1,5pentanediaminein in practice, and it is convenient for extending applications.

The descriptions illustrated supra set forth simply the preferred embodiments of the instant disclosure; however, the characteristics of the instant disclosure are by no means restricted thereto. All changes, alterations, or modifications conveniently considered by those skilled in the art are deemed to be encompassed within the scope of the instant disclosure delineated by the following claims.

What is claimed is:

1. An engineered bacteria, comprising:
   said engineered bacteria is an *Escherichia coli* (*E. coli*) strain B or its derivative strains with an overexpression of a lysine decarboxylase gene and a expression of a lysine-cadaverine antiporter gene cadB;
   said overexpression of said lysine decarboxylase gene is to place a complete and a partial nucleotide sequences of a modified lysine decarboxylase gene behind a promoter and a ribosomal binding site (RBS) in an exogenous expression plasmids for an expression;
   said lysine decarboxylase gene is a modified lysine decarboxylase gene, wherein said modified lysine decarboxylase gene is a cadA gene, a modification is to replace a second codon of a lysine decarboxylase gene cadA with a frequent second codon of said *E. coli*, and then to replace a No. +7_to +33 base sequence of lysine decarboxylase gene cadA (SEQ ID No.1) with synonymous codons; and
   said expression of said lysine-cadaverine antiporter gene is to place said complete and said partial nucleotide sequences of said lysinecadaverine antiporter gene with/without a RBS sequence behind said nucleotide sequences of said lysine decarboxylase gene in said exogenous expression plasmids for said expression; or, to replace a promoter of said lysinecadaverine antiporter gene on a chromosome of said *E. coli* strain B and said its derivative strains with said promoter capable of relieving a transcriptional repression of said CadB gene and suitable for said *E. coli*.

2. The engineered bacteria according to claim 1, wherein:
   said promoter, which is capable of relieving said transcriptional repression of said CadB gene and suitable for said *E. coli*, is selected from L promoter, trc promoter, T5 promoter, lac promoter, or T7 promoter.

3. The engineered bacteria according to claim 1, wherein:
   a No. +1 to +35 base sequence of said modified lysine decarboxylase gene cadA are as follows:

(the residues 7-41 of SEQ ID NO. 10)
   5'-ATGGCAGTTATAGCAATATTGAATCATATGGGAGT-3'

(the residues 7-41 of SEQ ID NO. 11)
   5'-ATGGCAGTTATAGCAATATTGAATCACATGGGGGT-3'

(the residues 7-41 of SEQ ID NO. 12)
   5'-ATGGCAGTTATAGCAATATTAAATCACATGGGGGT-3'

(the residues 7-41 of SEQ ID NO. 13)
   5'-ATGGCAGTTATTGCAATATTGAATCACATGGGAGT-3'

(the residues 7-41 of SEQ ID NO. 14)
   5'-ATGGCAGTTATTGCAATATTGAATCATATGGGAGT-3'

(the residues 7-41 of SEQ ID NO. 15)
   5'-ATGGCAGTTATTGCAATATTGAATCACATGGGGGT-3'

(the residues 7-41 of SEQ ID NO. 16)
   5'-ATGGCAGTTATTGCAATATTAAATCACATGGGGGT-3'

(the residues 7-41 of SEQ ID NO. 17)
   5'-ATGGCAGTTATTGCAATATTAAATCATATGGGAGT-3'.

4. The engineered bacteria according to claim 1, wherein:
   said *Escherichia coli* strain B is an *Escherichia coli* BL21 (DE3).

5. A method for preparing a 1, 5Pentanediamine, comprising following steps: culturing an engineered bacteria in a LB liquid medium containing a kanamycin, and obtaining a seed solution; inoculating said seed solution into a rich medium for a fermentation culture; and adding an inducer to induce an expression, and adding a substrate lysine and a vitamin B6 directly into said rich medium or adding said substrate lysine and said vitamin B6 after said engineered bacteria being collected and removed from said rich medium to initial a whole cell catalysis;
   wherein, said inducer is an IPTG or a lactose;
   wherein, said substrate lysine is a lysine fermentation broth containing a lysine producing bacteria, a bacterial cells removed lysine fermentation broth, a decolored bacterial cells removed lysine fermentation broth, an ion exchange elution of said lysine fermentation broth, a free lysine, and a lysine powder or a lysine solution;
   wherein, said vitamin B6 is a pyridoxal, a pyridoxal phosphate and/or a pyridoxal hydrochloride;
   wherein, said rich medium contains: 10 g/L yeast extract, 20 g/L peptone, 0.9 g/L $K_2HPO_4.3H_2O$, 1.14 g/L $KH_2PO_4$, 10 g/L $(NH_4)_2SO_4$, 0.3 g/L $MgSO_4.7H_2O$, 5 mL/L trace elements stock solution, 50 mg/L kanamycin, and water for the rest;
   wherein, said trace elements stock solution contains: 6 g/L $FeSO_4.7H_2O$, 1.35 g/L $CaCl_2$, 0.8 g/L $ZnSO_4.7H_2O$, 1.5 g/L $MnSO_4.4H_2O$, 0.15 g/L $CuSO_4.5H_2O$, 0.2 g/L $(NH_4)_6Mo_7O_{24}.4H_2O$, 0.1 g/L $H_3BO_3$, 0.25 g/L $CoCl_2.6H_2O$, 10 mL/L HCl (concentrated), and water for the rest.

6. The method for preparing the 1, 5Pentanediamine according to claim 5, wherein:
   a concentration of said kanamycin in said LB liquid medium is in a range of 5200 mg/L, and specifically is 50 mg/L;
   an $OD_{600}$ value of said seed solution is in a range of 225, and preferably is in a range of 35;
   said seed solution is inoculated into said rich medium by a volume percentage as in a range of 0.530%, and specifically is 5%;
   a fermentation temperature is in a range of 25° C. 45° C., and specifically is 37° C.;
   a DO of a fermentation culture is above 50%;
   a pH value of said fermentation culture is in a range of 4.09.0;
   a final concentration of said IPTG is in a range of 0.0110 mM, and preferably is in a range of 0.050.4 mM;
   a time of adding said IPTG is in a range of 210 h after fermentation, and preferably is in a range of 26 h;
   said IPTG inducing includes a step of supplementing a glucose at a rate being in a range of 0.510 g/L, and specifically being 3 g/L;
   said lysine is a Llysine hydrochloride;
   a time of adding said substrate lysine and said vitamin B6 to initial said whole cell catalysis is in a range of 0.510 h after an induction, and preferably is in a range of 15 h;

a pH value in a catalytic process is maintained in a range of 4.0-10.0; and said catalytic process also includes following steps: supplementing a glucose at a rate being in a range of 0.5-10 g/L, conducting an aeration rate being in a range of 0-10 vvm, controlling a temperature being in a range of 25-60° C., and conducting a rotation speed being in a range of 0-1200 rpm.

7. A method for preparing a 1, 5-Pentanediamine, comprising following steps:

culturing an engineered bacteria in a LB liquid medium containing a kanamycin, and obtaining a seed solution; inoculating said seed solution into a minimal medium for a fermentation culture; and adding an inducer to induce an expression, and adding a substrate lysine and a vitamin B6 directly into said minimal medium, or adding said substrate lysine and said vitamin B6 after said engineered bacteria being collected and removed from said minimal medium to initial a whole cell catalysis;

wherein, said inducer is an IPTG or a lactose;

wherein, said substrate lysine is a lysine fermentation broth containing a lysine producing bacteria, a bacterial cells removed lysine fermentation broth, a decolored bacterial cells removed lysine fermentation broth, an ion exchange elution of said lysine fermentation broth, a free lysine, and a lysine powder or a lysine solution; and wherein, said vitamin B6 is a pyridoxal, a pyridoxal phosphate and a pyridoxal hydrochloride.

8. The method for preparing the 1, 5-Pentanediamine according to claim 7, wherein:

a concentration of said kanamycin in said LB liquid medium is in a range of 5-200 mg/L, and specifically is 50 mg/L;

an $OD_{600}$ value of said seed solution is in a range of 2-25, and preferably is in a range of 3-5;

a percentage of said minimal medium inoculated into said seed solution is in a range of 0.5-30%, and specifically is 2%;

a fermentation temperature is in a range of 25° C.-45° C., and specifically is 37° C.;

a DO of a fermentation culture is above 50%;

a concentration of a glucose during said fermentation culture is maintained below 5 g/L, in particular realized by adding a feeding fluid in a Fed-batch fermentation, said feeding fluid contains 700 g/L glucose and 20 g/L $MgSO_4 \cdot 7H_2O$, and water for the rest;

a final concentration of said IPTG is in a range of 0.01-10 mM, and preferably is in a range of 0.05-0.4 mM;

a time of adding said IPTG is in a range of 3-20 h after fermentation, and preferably is in a range of 4-12 h;

said lysine is a L-lysine hydrochloride;

a time of adding said substrate lysine and said vitamin B6 to initial said whole cell catalysis is in a range of 0.5-24 h after the induction, and preferably is in a range of 1-5 h;

a pH value of a catalytic process is maintained in a range of 4.0-10.0, and specifically is 6.5; and said catalytic process also includes following steps: supplementing said glucose at a rate being in a range of 0-50 g/L, conducting an aeration rate being in a range of 0-10 vvm, controlling a temperature being in a range of 25-60° C., and conducting a rotation speed being in a range of 0-1200 rpm.

9. The engineered bacteria according to claim 2, wherein:

a No. +1 to +35 base sequence of said modified lysine decarboxylase gene cadA are as follows:

```
              (the residues 7-41 of SEQ ID NO. 10)
5'-ATGGCAGTTATAGCAATATTGAATCATATGGGAGT-3'

(the residues 7-41 of SEQ ID NO. 11)
5'-ATGGCAGTTATAGCAATATTGAATCACATGGGGGT-3'

(the residues 7-41 of SEQ ID NO. 12)
5'-ATGGCAGTTATAGCAATATTAAATCACATGGGGGT-3'

(the residues 7-41 of SEQ ID NO. 13)
5'-ATGGCAGTTATTGCAATATTGAATCACATGGGAGT-3'

(the residues 7-41 of SEQ ID NO. 14)
5'-ATGGCAGTTATTGCAATATTGAATCATATGGGAGT-3'

(the residues 7-41 of SEQ ID NO. 15)
5'-ATGGCAGTTATTGCAATATTGAATCACATGGGGGT-3'

(the residues 7-41 of SEQ ID NO. 16)
5'-ATGGCAGTTATTGCAATATTAAATCACATGGGGGT-3'

(the residues 7-41 of SEQ ID NO. 17)
5'-ATGGCAGTTATTGCAATATTAAATCATATGGGAGT-3'.
```

10. The engineered bacteria according to claim 2, wherein: said *Escherichia coli* strain B is an *Escherichia coli* BL21 (DE3).

11. The engineered bacteria according to claim 3, wherein: said *Escherichia coli* strain B is an *Escherichia coli* BL21 (DE3).

* * * * *